United States Patent
Chen et al.

(10) Patent No.: US 10,668,012 B2
(45) Date of Patent: Jun. 2, 2020

(54) CHEWABLE SUSTAINED RELEASE FORMULATIONS

(75) Inventors: Andrew Xian Chen, San Diego, CA (US); Patricia D Kigin, Phoenix, AZ (US); Hai Liang Chen, San Diego, CA (US); Jun Fan, San Diego, CA (US)

(73) Assignee: Farnam Companies, Inc., Phoenix, AZ (US)

( * ) Notice: Subject to any disclaimer, the term of this patent is extended or adjusted under 35 U.S.C. 154(b) by 1008 days.

(21) Appl. No.: 12/554,361

(22) Filed: Sep. 4, 2009

(65) Prior Publication Data

US 2010/0062988 A1    Mar. 11, 2010

Related U.S. Application Data

(60) Provisional application No. 61/094,363, filed on Sep. 4, 2008.

(51) Int. Cl.
  *A61K 31/16*    (2006.01)
  *A61K 9/00*    (2006.01)
  *A61K 9/16*    (2006.01)
  *A61K 9/20*    (2006.01)

(52) U.S. Cl.
  CPC .......... *A61K 9/0056* (2013.01); *A61K 9/1658* (2013.01); *A61K 9/1664* (2013.01); *A61K 9/2063* (2013.01); *A61K 9/2068* (2013.01)

(58) Field of Classification Search
  None
  See application file for complete search history.

(56) References Cited

U.S. PATENT DOCUMENTS

| | | | | |
|---|---|---|---|---|
| 3,567,819 A | * | 3/1971 | Idson | 424/441 |
| 5,032,406 A | * | 7/1991 | Dansereau et al. | 424/472 |
| 5,077,053 A | * | 12/1991 | Kuncewitch et al. | 424/441 |
| 5,182,130 A | * | 1/1993 | Haralampu et al. | 427/2.14 |
| 5,188,841 A | | 2/1993 | Simpkin et al. | 424/495 |
| 5,599,556 A | * | 2/1997 | Meyer et al. | 424/491 |
| 5,904,937 A | * | 5/1999 | Augello | A61K 9/0056 |
| | | | | 424/441 |
| 6,210,714 B1 | * | 4/2001 | Oshlack et al. | 424/476 |
| 6,277,409 B1 | * | 8/2001 | Luber et al. | 424/476 |
| 6,436,438 B1 | | 8/2002 | Momberger et al. | 424/458 |
| 6,699,506 B1 | | 3/2004 | Paillard et al. | 424/489 |
| 6,723,358 B1 | * | 4/2004 | van Lengerich | A61K 9/0056 |
| | | | | 424/439 |
| 6,897,205 B2 | | 5/2005 | Beckert et al. | 514/159 |
| 2003/0124184 A1 | * | 7/2003 | Mezaache et al. | 424/465 |
| 2003/0228368 A1 | | 12/2003 | Wynn et al. | 424/486 |
| 2005/0089558 A1 | | 4/2005 | Cutler | 424/464 |
| 2006/0153908 A1 | | 7/2006 | Strong et al. | 424/451 |

FOREIGN PATENT DOCUMENTS

| | | |
|---|---|---|
| EP | 1 900 283 A2 | 3/2008 |
| GB | 2 403 407 A | 1/2005 |
| JP | 2008-035730 | 2/2008 |
| WO | WO 96/14058 | 5/1996 |
| WO | WO 02/043706 A2 | 6/2002 |
| WO | 2006/082824 A1 | 8/2006 |

OTHER PUBLICATIONS

O'Donnell. European Journal of Pharmaceutics and Biopharmaceutics. 43 (1997) 83-89.*
Pulmonary. http://www.mupeg.com/p_pulmonary_nightandday_01.htm. Published in 2002.*
Proin. http://www.allivet.com/p-1204-proin.aspx. Published Aug. 27, 2004.*
Jivaraj. PSTT vol. 3, No. 2 Feb. 2000.*
Yixiang et al., "Multiple Dose Bioavailability Comparison Between Phenylpropa-Nolaminecontrolled-Release Suspension and Conventional Tablet in Healthy Volunteers," Chinese Journal of Clinical Pharmacy, 1994, vol. 3(1), pp. 13-15.

* cited by examiner

*Primary Examiner* — Tigabu Kassa
(74) *Attorney, Agent, or Firm* — Kilpatrick Townsend & Stockton LLP

(57) ABSTRACT

Sustained release compositions in tablet or multiparticulate forms comprising (a) an active ingredient, (b) a primary sustain release agent, (c) a wax-like agent, and (d) a bulking or spheronizing agent are provided. The compositions are chewable and/or taste masked. Oral dosage forms comprising such compositions and methods for preparing and using such compositions and dosage forms are also provided.

4 Claims, 16 Drawing Sheets

CHEWABLE SUSTAINED RELEASE FORMULATIONS

CROSS-REFERENCE TO RELATED APPLICATION

This application claims the benefit under 35 U.S.C. § 119(e) of U.S. Provisional Patent Application No. 61/094,363, filed Sep. 4, 2008, where this provisional application is incorporated herein by reference in its entirety.

BACKGROUND

Technical Field

This disclosure relates to chewable and sustained release compositions and dosage forms and to methods of preparing and using such compositions and dosage forms.

Description of the Related Art

A chewable pharmaceutical dosage is defined as a drug composition that retains certain drug release and taste properties even after it has been chewed into smaller fragments. Chewable pharmaceutical dosage forms are of particular interest for companion animal veterinary applications because the patients (e.g., dogs, cats, horses etc.) tend to chew any dosage form that is given orally. In human medicine, chewable dosage forms are preferred for young or senior patients who have difficulties in swallowing intact tablets or capsules.

Many drugs or pharmaceutically active ingredients require specific release kinetics such as a prolonged release, including drugs that have a short half-life and those that require sustained blood plasma levels. Sustained release formulations are developed to avoid multiple daily dosing and lack of, or reduced, patient compliance. Such formulations are also more preferably applied for patients on chronic medication.

Tablets are by far the most popular sustained release dosage form. Generally, sustained release tablets have been prepared in two ways: matrix and coated tablets. In a matrix tablet, the drug is usually mixed with a polymeric gelling material, which upon contact with water can form a thick layer of gel that slows down the diffusion of the drug while undergoing slow erosion. Both diffusion and erosion contribute to drug release. A coated tablet relies on small pores in the coating to control the drug release from its core.

The existing sustained release tablet compositions, whether matrix or coated, are not suitable as a chewable formulation, as they rely on matrix or coating to be intact for the drug release control. Chewing will destroy easily the integrity of the matrix or coating, and result in an uncontrolled drug burst or overdose and many times, unacceptable taste. Certain animals, such as cats, are extremely sensitive to taste and will not accept any dosage form voluntarily that has unfavorable taste. Accordingly, there is still a need for developing sustained release tablets that better retain the sustained release capability and certain taste masking property after being chewed or fragmented.

Other common dosage forms for oral administration to animal or human patients with swallowing limitation are multiparticulates that comprise a multiplicity of drug-containing particles whose totality represents the intended therapeutically useful dose of a drug. A multiparticulate formulation may be represented by other terms such as powders, granules, pellets, microspheres, minispheres, beadlets, sachets etc. It may be dosed as (1) dry powder which is administered orally and swallowed with liquid, (2) dispersed in a liquid and then swallowed, or (3) placed in a capsule.

For the first and second methods of administration, large amounts of particles can be administered. For example, 5-10 grams of spherical pellets can be suspended in water and swallowed easily by a human patient. For animals such as horse, a multiparticulate formulation can be readily mixed with feed and consumed voluntarily, provided the taste is acceptable.

Numerous active ingredients require sustained release kinetics or prolonged release such as twice-a-day, preferably once-a-day, or ever more preferable once every 2-3 days. In such instances, use is made of so-called sustained release multiparticulate formulations. Known sustained release multiparticulate formulations rely almost exclusively on a thick coating system to provide a barrier to the drug release, i.e., "sustained release coating." This is due to the greatly increased surface area of the small particles compared to a tablet. This great increase in surface area and fast dissolution have made sustained release particles or spheres almost impossible without the barrier coating (see, U.S. Patent Application Publication No. 2006/0153908, U.S. Pat. Nos. 5,188,841, 6,699,506, 6,897,205, and 6,436,438). The sustained release coating prevents the multiparticulate formulations form being used as a chewable dosage form because chewing would destroy the coating and result in drug burst and poor taste. Therefore, there is need for new multiparticulate compositions that can sustain certain chewing while maintaining a sustained release and certain taste masking properties.

BRIEF SUMMARY

The present disclosure provides chewable and sustained release pharmaceutical compositions in tablet and multiparticulate dosage forms for pharmaceutically active ingredients, especially those with short half-lives, and methods for preparing and using such pharmaceutical compositions.

The pharmaceutical compositions provide sustained release of active ingredients that does not require a sustained release barrier coating. Such compositions of the present disclosure may be in the form of tablets or multiparticulate dosage forms, and retain sustained release of active ingredients even when they are chewed or fragmented into smaller pieces. Such a property facilitates administering drugs to young or senior patients who have difficulties in swallowing intact tablets and for ease of dosing animal patients that prefer a chewable dosage form.

In certain embodiments, the tablet compositions of the present disclosure have a sustained release property with a minimal initial burst of active ingredients (e.g., no greater than 5% during the first 1 to 5 minutes in an in vitro dissolution test), even after being broken into smaller pieces. Such a feature allows the making of a chewable tablet formulation and yet maintaining the sustained release property.

In other embodiments, the multiparticulate compositions of the present disclosure, surprisingly, have provided a high level of taste masking property for some extremely bitter drugs such as tramadol, and such compositions were well accepted and voluntarily consumed orally by cats, which are regarded as the most sensitive and picky eaters and are probably the most difficult patients to treat with respect to voluntary drug administration.

In yet other embodiments, the multiparticulate compositions of the present disclosure, surprisingly, have provided a sustained release property for highly water soluble drugs, even without coating.

In another aspect, the present disclosure provides a final dosage form that comprises the chewable and sustained release multiparticulate composition as provided herein.

In another aspect, the present disclosure provides methods for preparing the multiparticulate compositions as provided herein in the form of granulates, extrudates, noodles, non-spherical pellets, or spherical pellets via extrusion or wet granulation process.

The compositions of the present disclosure are useful in treating or preventing various diseases or disorders for that the active ingredients in the compositions are effective (e.g., treating incontinence or congestion, suppressing appetite, reducing pain, and treating or preventing a chronic disease or a dietary deficiency).

DETAILED DESCRIPTION

Figure 1:
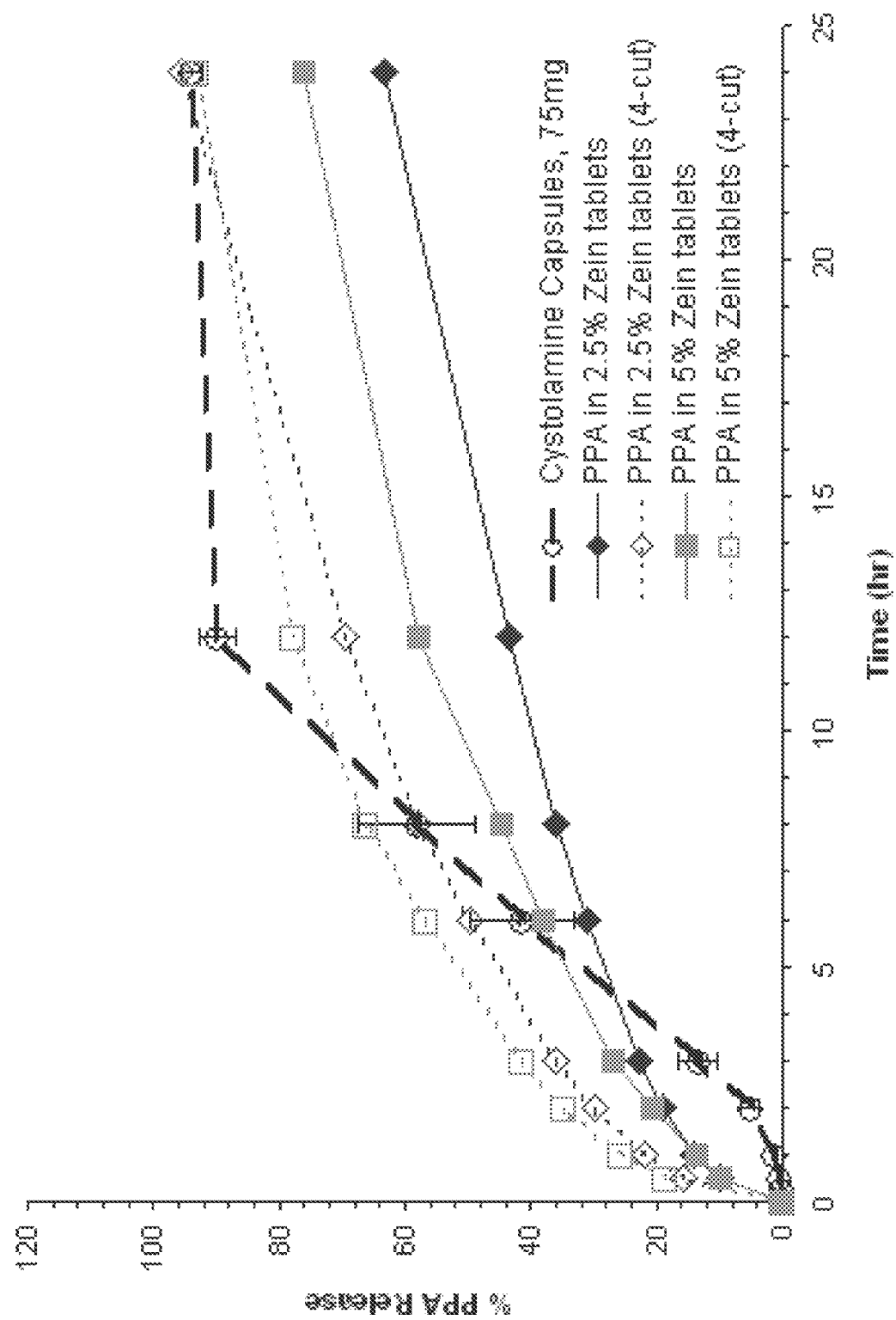
FIG. 1 shows in vitro dissolution profiles of 75 mg phenylpropanolamine (PPA) HCl sustained release tablets at two different zein concentrations, as compared to CYS-TOLAMINE® capsules, 75 mg.

The present disclosure provides chewable pharmaceutical compositions for sustained release of pharmaceutically active ingredients, especially those with short half-lives, and methods for preparing and administering such pharmaceutical compositions.

Unless indicated otherwise, any percentage is weight by weight (w/w) relative to the total weight of a composition, to the total weight of a tablet, or to the total weight of a pellet.

As used in the present disclosure, the term "about" refers to any value in the range of 90% to 110% of a specified value. For example, about 40° C. refers to any temperature from 36° C. to 44° C.

As used in the present disclosure, any numerical ranges recited herein are to be understood to include any integer within the range and, where applicable (e.g., concentrations), fractions thereof, such as one tenth and one hundredth of an integer (unless otherwise indicated).

I. Compositions

In one aspect, the present disclosure provides a composition that (a) comprises, consists essentially of, or consists of (i) an active ingredient, (ii) a primary sustained release agent, (iii) a wax-like agent, and (iv) a bulking or spheronizing agent; (b) is in the form of tablets or multiparticulates; and (c) provides sustained release of the active ingredient that does not require the presence of a sustained release barrier coating on the tablets or multiparticulates. In certain embodiments, the compositions provided herein retain sustained release of active ingredients even when they are chewed or fragmented into smaller pieces. In certain embodiments, the compositions of the present disclosure have minimal initial burst of active ingredients to enable the making of taste masking formulations (e.g., pellets or tablets).

A. Active Ingredients

The active ingredients in the composition may be any pharmaceutically active ingredients (i.e., a compound or a composition, such as an herb extract, with beneficial pharmaceutical, therapeutic, nutritional, or cosmetic effects).

In certain embodiments, the active ingredient is phenylpropanolamine or its pharmaceutically acceptable salt (e.g., phenylpropanolamine hydrochloride). Phenylpropanolamine has been used in human as a decongestant and also as an appetite suppressant. In veterinary medicine, it is used to control urinary incontinence in dogs.

In certain embodiments, the active ingredient may be an analgesic or a pharmaceutically acceptable salt thereof, such as acetaminophen, a centrally acting analgesic agent, opiate, narcotic, nonsteroidal anti-inflammatory drugs (NSAIDs), and salicylate. In certain embodiments, the active ingredient is a combination of two or more analgesics or their pharmaceutically acceptable salts thereof. In certain embodiments, the analgesic is tramadol or a pharmaceutically acceptable salt thereof (e.g., tramadol HCl).

Exemplary NSAIDs that may be used as the active ingredient in the present compositions include, and are not limited to, aspirin, carprofen, deracoxib, etodolac, firocoxib, celecoxib, diclofenac, diflunisal, fluriprofen, ibuprofen, indomethacin, ketoprofen, kietorolac, mefenamic acid, meloxicam, naproxen, phenylbutazone, piroxicam, rofecoxib, sulindac, tepoxalin, valdecoxib, and vedaprofen.

In certain embodiments, the active ingredient is a dietary supplement or nutraceutical, such as vitamins (e.g., vitamin C and B complex), multi-vitamins (i.e., a mixture of multiple vitamins, such as a mixture of two or more fat-soluble vitamins, a mixture of two or more water soluble vitamins, and a mixture of one or more fat-soluble vitamins and one or more water-soluble vitamins), minerals, herbs or other botanicals, amino acids, proteins (e.g., milk protein concentrates, including ImmuSyn and Microlatin), anti-oxidants (e.g., grape seed extract and milk thistle), anti-inflammatory agents (e.g., bromelain), carotenoids (e.g., lycopene and lutein), flavonoids (e.g., quercetin and rutin), prebiotics (e.g., arabinogalactan—a water soluble polysaccharide, and fructooligosaccharides), weight loss agents (e.g., garcinia cambogia), and other nutrient substances or their constituents. In certain embodiments, the dietary supplement or nutraceutical is glucosamine or a pharmaceutically acceptable salt thereof (e.g., glucosamine hydrochloride). In certain embodiments, the dietary supplement or nutraceutical is chondroitin sulfate. In certain embodiments, the active ingredient is a combination of two or more dietary supplements or nutraceuticals. For example, the active ingredient may be the combination of glucosamine hydrochloride and chondroitin sulfate.

In certain embodiments, the active ingredient is an anti-infective or anti-microbial agent or a pharmaceutically acceptable salt thereof, such as antibiotics (including β-lactam antibiotics (e.g., amoxicillin, ampicillin, ceftiofur), lincosamides (e.g., clindamycin), aminoglycosides, cephalosporins, macrolides, ketol ides, penicillins, quinolones, sulfonamides, tetracyclines (e.g., doxycycline), cycloserine, vancomycin, linezolid, oxazolidinone, pyrimethamine, atovaquone, tigecycline, glycylcyclines), anthelmintics, antifungals, antimalarial, antiprotozoal agents, leprostatics, antituberculosis agents, and anti-parasitics. In certain embodiments, the anti-infective agent is azithromycin, clarithromycin, roxithromycin, erythromycin, telithromycin, ciprofloxacin, a combination of amoxicillin and clavulanate potassium, or a pharmaceutically acceptable salt thereof. In certain embodiments, the active ingredient is a combination of two or more anti-infective or anti-microbial agents or their pharmaceutically acceptable salts.

In certain embodiments, the active ingredient is a thyroid or a thyroid modulating agent, including levothyroxine sodium useful for treating hypothyroidism and methimazole useful for treating hyperthyroidism.

In certain embodiments, the active ingredient is a behavior modifying drug, such as anti-anxiety agents and antidepressants. Exemplary behavior modifying drugs include, and are not limited to, buspirone hydrochloride, fluoxetine hydrochloride, paroxetine, amitriptyline hydrochloride, clomipramine hydrochloride, doxepin, and imipramine hydrochloride.

In certain embodiments, the active ingredient is an anti-diabetic agent. Exemplary anti-diabetic agents include, but are not limited to, glipizide, metformin, acarbose, and glibenclamide.

In certain embodiments, the active ingredient is a phosphate binding compounds. Exemplary compounds include, but are not limited to, sevelamer hydrochloride, aluminum carbonate, and aluminum hydroxide.

In certain embodiments, the active ingredient is an antiviral agent or a pharmaceutically acceptable salt thereof, such as abacavir, acyclovir, ganciclovir, lammivudine, nelfinavir, ritonavir, valacyclovir, and zidovudine. In certain embodiments, the active ingredient is a combination of two more antiviral agents or their pharmaceutically acceptable salts.

In certain embodiments, the active ingredient is an antacid, such as sodium antacids (e.g. trisodium phosphate, also referred to as "sodium phosphate tribase"), calcium antacids (e.g. calcium carbonate, aluminum antacids (e.g., aluminum hydroxide), magnesium antacids (e.g., magnesium hydroxide), and combinations thereof. In certain embodiments, the antacid is aluminum hydroxide, magnesium hydroxide, trisodium phosphate (also referred to as "sodium phosphate tribase") or a combination of two or all of these three compounds. In certain embodiments, the antacid is a combination of aluminum hydroxide and magnesium hydroxide, or a combination of trisodium phosphate and magnesium hydroxide at a weight ratio of about 1:3, 1:2, 1:1, 2:1, or 3:1.

In certain embodiments, the active ingredient is an insect growth regulator (IGR) or a pharmaceutically acceptable salt thereof, such as methoprene, kinoprene, hydroprene, diflubenzuron, or pyriproxifen. In certain embodiments, the active ingredient is a combination of two or more insect growth regulators or their pharmaceutically acceptable salts.

In certain embodiments, the active ingredient is an antioxidant or a pharmaceutically acceptable salt thereof, such as ascorbic acid, bromelain, grapeseed extract, milk thistle, rose hip, alpha lipoic acid, beta carotene, lycopene, lutein and alpha tocopherol. In certain embodiments, the active ingredient is a combination of two or more antioxidants or their pharmaceutically acceptable salts.

A "pharmaceutically acceptable salt" of a pharmaceutically active ingredient refers to a salt (including an acid addition salt) of the pharmaceutically active ingredient, within the scope of sound medical judgment, suitable for use in contact with the tissues of humans and lower animals without undue toxicity, irritation, allergic response, and the like, and effective for the intended use of the pharmaceutically active ingredient.

In certain embodiments, the active ingredient is a high dose pharmaceutically active ingredient. A pharmaceutically active ingredient of "high dose" refers to a pharmaceutically active ingredient that is orally administered at a daily dose of about or greater than 1 mg/kg body weight to an adult human patient or an adult non-human subject (e.g., a dog, cat, horse, pig, etc.). In certain embodiments, the pharmaceutically active ingredient of the present disclosure has a daily dose about or greater than 2, 3, 4, 5, 6, 7, 8, 9, 10, 20, 30, 40, or 50 mg/kg body weight for an adult human or an adult non-human subject. In certain embodiments, the pharmaceutically active ingredient of the present disclosure has a daily dose about or greater than 100, 200, 250, 300, 350, 400, 450, 500, 600, 700, 800, 900, or 1000 mg for an adult human or an adult non-human subject. In certain embodiments, the active ingredients are those that must be given at about 200 mg, 300 mg, 400 mg, 500 mg, 600 mg, 700 mg, 800 mg, 900 mg, or 1 g per dose in a twice-a-day, once-a-day or once-per-treatment regimen.

Exemplary pharmaceutically active ingredients of high dose include tramadol (e.g., tramadol HCl) (100 mg/dose or more), acyclovir (200 mg/dose), acetaminophen (300 mg/dose), metformin (e.g., metformin HCl) (500 mg/dose), gabapentin (100-800 mg/dose), glucosamine, glucosamine sulfate, and glucosamine HCl (500 mg/dose).

In certain embodiments, the active ingredient has a short half-life. A pharmaceutically active ingredient of "short half-life" refers to a pharmaceutically active ingredient that has a half-life about or less than 12 hours. In certain embodiments, the pharmaceutically active ingredient of the present disclosure has a half-life of about or less than about 11, 10, 9, 8, 7, 6, 5, 4, 3, or 2 hours in a human (e.g., an adult human patient) or non-human subject (e.g., a dog, cat, horse, pig, etc.). In general, a pharmaceutically active ingredient of a short half-life is required to be taken more than twice a day in its immediate release forms to maintain the efficacious blood concentration level through the day.

In certain embodiments, the active ingredient may be insoluble, slightly soluble, sparingly soluble, soluble, freely soluble or very soluble in water. These terms are defined in Remington's Pharmaceutical Sciences, Mack Publishing Co., Easton, Pa., the latest edition.

In certain embodiments, the active ingredient is present in an amount of at least about 0.1%, 1%, 5%, 10%, 15%, 20%, 25%, 30%, 35%, 40%, 45%, or 50%, 55%, or 60% of the total weight of the composition. In certain embodiments, the active ingredient is present in an amount of at most about 65%, 70%, 75%, 80%, 85%, 90%, or 95% of the total weight of the composition. In certain embodiments, the active ingredient is present in the range of from about 0.1% to about 95%, such as from about 1% to about 90%, about 1% to about 80%, about 1% to about 70%, about 1% to about 60%, about 1% to about 50%, about 1% to about 40%, about 1% to about 30%, about 1% to about 20%, about 1% to about 10%, about 2% to about 50%, about 3% to about 25%, about 0.5% to about 20%, about 10% to about 60%, about 10% to about 50%, about 10% to about 40%, about 10% to about 30%, about 10% to about 20%, about 20% to about 60%, about 20% to about 50%, about 20% to about 40%, about 20% to about 30%, about 30% to about 60%, about 30% to about 50%, about 30% to about 40%, about 40% to about 60%, about 40% to about 50%, about 25% to about 75%, about 50% to about 80%, about 5% to about 30%, about 0.5% to about 20%, or any other ranges between any one of the above-noted minimum amount and any one of the above-noted maximum amount, w/w relative to the total weight of the composition.

In certain embodiments, the composition may further comprise a second pharmaceutically active ingredient. In certain embodiments, the second pharmaceutically active ingredient may be of high dose and/or short half-life. For example, in certain embodiments, the active ingredient may comprise glucosamine hydrochloride and chondroitin sulfate; tramadol hydrochloride and glucosamine hydrochloride; glucosamine HCl, chondroitin, calcium ascorbate, and manganese sulfate; or tramadol hydrochloride and acetaminophen.

In certain embodiments, the other pharmaceutically active ingredient may have a same or similar pharmaceutical effect as the first pharmaceutically active ingredient in a pharmaceutical composition. For instance, a pharmaceutical composition of the present disclosure may comprise tramadol and another analgesic agent. In certain embodiments, the second pharmaceutically active ingredient may have a pharmaceutical effect different from the first pharmaceutically active ingredient. For instance, a pharmaceutical composition of the present disclosure may comprise glucosamine, chondroitin, manganese sulfate and calcium ascorbate.

In certain embodiments, the pharmaceutical composition comprises tramadol and another analgesic agent. For example, in certain embodiments, the pharmaceutical composition comprises tramadol and an opioid analgesic. In certain other embodiments, the pharmaceutical composition comprises tramadol and a non-steroidal anti-inflammatory drug (NSAID).

B. Primary Sustained Release Agents

The compositions of the present disclosure also comprise a primary sustained release agent that is a pharmaceutically acceptable material capable of forming tablets or multiparticulates with an active ingredient, a wax-like agent, and a bulking or spheronizing agent, and providing sustained release of the active ingredient.

A "primary sustained release agent," as used herein, refers to an aqueous solution or dispersion of a water-insoluble polymer, such as zein and ethylcellulose. Exemplary primary sustained release agents include, and are not limited to, AQUA ZEIN®, AQUA COAT®, and SURELEASE®. AQUA ZEIN® is an aqueous dispersion of zein. Zein is an insoluble protein derived from corn. In AQUA ZEIN®, zein is made soluble in water using ammonia and propylene glycol. Both AQUA COAT® and SURELEASE® are aqueous ethylcellulose dispersions. Ethylcellulose is insoluble in water and is made to dissolve or disperse in water by ammonia and/or surfactant in AQUA COAT® and SURELEASE®. In certain embodiments, the primary sustained release agent includes enriched AQUA ZEIN® (i.e., an aqueous dispersion of zein with a higher concentration of zein than commercially available AQUA ZEIN®, such as by dissolving additional zein in AQUA ZEIN®). The primary sustained release agent does not include solid polymers or solutions of polymers in organic solvents.

In certain embodiments, a primary sustained release agent is first mixed with an active ingredient. Such mixture is subsequently mixed with a wax-like material, and a bulking or spheronizing agent to form wet granules, which are then dried and heated to a temperature exceeding the melting point of the wax-like agent to form a chewable, sustained release and taste-masked multiparticulate composition.

In other embodiments, the resulting sustained release and taste-masked multiparticulate composition is further embedded in a tablet matrix to form a chewable tablet.

Without wishing to be bound by any theory, it is believed that two mechanisms are involved in the composition of this disclosure to provide chewable, sustained release and taste-masked properties. The first mechanism is based on the formation of an insoluble solid matrix ("core") of the active ingredient by the primary sustained release agent. The primary sustained release agent "seals" the active ingredient by embedding the active ingredient in the core. However, the insoluble solid matrix core alone did not seem to have sufficient sustained release or taste-masking property for a chewable dosage form. A secondary mechanism is thus added by using the wax-like agent, which provides additional sustained release or taste-masking property to the core possibly by forming a barrier around the core and by sealing the cracks and crevasses in the core with a hydrophobic material. This "double sealing" process results in a surprisingly high degree sustained release and task-masking property, even after the composition being chewed or broken into smaller pieces.

The tablets or multiparticulate compositions of the present disclosure by the double sealing process are different from those where the primary sustained release agent or the wax-like agent is used individually, which did not provide sufficient taste-masking properties as a chewable dosage and were not accepted by cats for voluntarily consumption. For clarification, the primary sustained release agents of this disclosure are not used as coating materials or used solely as coating materials, although AQUA ZEIN®, AQUA COAT®, and SURELEASE® are traditionally used as coating materials.

In certain embodiments, the primary sustained release agent is present in the composition in an amount of about 0.5% to about 30%, about 0.5% to about 20%, about 0.5% to about 10%, such as about 1% to about 25%, about 1% to about 20%, about 1% to about 15%, about 1% to about 10%, about 1% to about 8%, about 1% to about 5%, and about 2% to about 5%, of the total weight of the composition. In certain embodiments, the primary sustained release agent is present in an amount of about 1%, 1.5%, 2%, 2.5%, 3%, 3.5%, 4%, 4.5%, 5%, 5.5%, 6%, 6.5% or 7% of the total weight of the composition.

C. Wax-Like Agents

A "wax-like agent," as used herein, refers to a natural, semi-synthetic or synthetic material that is plastic (i.e., malleable) at normal ambient temperatures (i.e., 20-25° C.), has a melting point above 40° C., is very slightly soluble, practically insoluble, or insoluble in water (e.g., having a water-solubility lower than about 1:5000 (w/w)), and is composed of an ester of a fatty alcohol and saturated and unsaturated fatty acid(s), saturated and unsaturated fatty acid glyceride (mono-, di- or triglyceride), hydrogenated fat, hydrogenated vegetable oil, cholesterol, hydrocarbon, hydrophobic polymer having a hydrocarbon backbone, hydrophilic polymer having a hydrocarbon backbone, or a combination of one or more of the above-listed compounds.

A wax-like agent, as used herein, includes commonly known wax, such as animal and insect waxes (e.g., beeswax, Chinese wax, shellac wax, spermaceti wax, lanolin wax), vegetable waxes (e.g., bayberry wax, candelilla wax, carnauba wax, castor wax, esparto wax, Japan wax, jojoba oil, ouricury wax, rice bran wax), mineral waxes (e.g., ceresin waxes, montan wax extracted from lignite and brown coal, ozocerite, peat waxes), petroleum waxes (e.g., paraffin wax, microcrystalline wax), and synthetic waxes (e.g., polyethylene waxes, Fischer-Tropsch waxes, chemically modified waxes (e.g., esterified or saponified waxes), substituted amide waxes, and polymerized α-olefins). In certain embodiments, the wax is an ester of ethylene glycol and two fatty acids.

In certain embodiments, the wax-like agent is thermoplastic with a melting point above 40° C. (e.g., above 45° C.), and below 120° C. (e.g., below 110° C.), including any value between 40° C. and 120° C. In certain embodiments, the wax-like agent has a melting point in a range formed by any two values between 40° C. and 120° C., such as between 50° and 100° C. In certain embodiments, the wax-like agent is hydrogenated vegetable oils, such as hydrogenated cottonseed oil, partially hydrogenated cottonseed oil, hydrogenated soybean oil, partially hydrogenated soybean oil, and stearyl alcohol.

In certain other embodiments, the wax-like agent is vegetable wax, such as bayberry wax, candelilla wax, carnauba wax, castor wax, esparto wax, Japan wax, jojoba oil, ouricury wax, rice bran wax In certain embodiments, the wax-like agent is present in the composition in an amount of at least about 1%, 2%, 3%, 4%, 5%, 6%, 7%, 8%, 9%, 10%, 15%, or 20% of the total weight of the composition. In certain embodiments, the wax-like agent is present in an amount of at most about 30%, 35%, 40%, 45%, 50%, 60%, 70%, or 80% of the total weight of the composition. In certain embodiments, the wax-like agent is present in the range of from about 1% to about 80%, such as from about 10% to about 80%, from about 1% to about 70%, from about 1% to about 35%, from about 1% to about 15%, from about 5% to about 55%, from about 15% to about 35%, from about 20% to about 80%, from about 40% to about 65%, from about 20% to about 70%, from about 40% to about 60%, or any range between any one of the above-noted minimum amount and any one of the above-noted maximum amount, w/w relative to the total weight of the composition.

D. Bulking or Spheronizing Agents

A "bulking agent," as used herein, refers to an agent that increases the mass of an individual dose to a size suitable for tablet compression. In certain embodiments, a bulking agent is capable of forming, together with an active ingredient, a primary sustained release agent, and a wax-like agent, a cohesive plastic mass that may be subsequently granulated or extruded and then compressed into tablets.

A "spheronizing agent," as used herein, refers to an agent that together with an active ingredient and a wax-like agent, forms a cohesive plastic mass that may be subsequently spheronized to produce spherical pellets or fragmented to form non-spherical pellets.

In certain embodiments, the bulking or spheronizing agent is microcrystalline cellulose, such as the product sold under the tradename "AVICEL™." Other exemplary bulking or spheronizing agents include starch, sodium carboxymethylcellulose, and pregelatinized starch (e.g., pregelatinized corn starch). In certain embodiments, the bulking or spheronizing agent is a combination of microcrystalline cellulose and pregelatinized starch.

Additional exemplary bulking or spheronizing agents include powdered sugar, calcium phosphate, calcium sulfate, lactose, mannitol, kaolin, sodium chloride, dry starch, sorbitol, etc.

In certain embodiments, the bulking or spheronizing agent (e.g., microcrystalline cellulose or a combination of microcrystalline cellulose and pregelatinized starch) is present in the composition in an amount of at least about 1%, 2%, 3%, 4%, 5%, 6%, 7%, 8%, 9%, 10%, 12%, 14%, 16%, 18%, 20%, 22%, or 25% of the total weight of the composition. In certain embodiments, the bulking or spheronizing agent is present in an amount of at most about 50%, 55%, 60%, 65%, 70%, 75%, or 80% of the total weight of the composition. In certain embodiments, the bulking or spheronizing agent is present in the range from about 5% to about 70%, such as from about 5% to about 25%, from about 10% to about 40%, from about 10% to about 50%, from about 15% to about 35%, from about 15% to about 45%, from about 15% to about 65%, from about 20% to about 55%, from about 20% to about 60%, from about 25% to about 55%, from about 30% to about 50%, or any range between any one of the above-noted minimum amount and any one of the above-noted maximum amount, w/w relative to the total weight of the composition.

E. Sustained Release

The composition of the present disclosure provides sustained release of the active ingredient.

The term "sustained release," as used in describing the present disclosure, refers to the release of the active ingredient more slowly than that from an immediate release dosage form. The term may be used interchangeably with "slow-release," "controlled release," or "extended release." The sustained release property of a composition is typically measured by an in vitro dissolution method and confirmed by an in vivo blood concentration-time profile (i.e., a pharmacokinetic profile).

The term "immediate release dosage forms" refers to release forms wherein at least 75% of the active ingredient is released or dissolved within about one-half hour after in vivo administration or in an in vitro dissolution assay as known in the art or provided herein.

In certain embodiments, the pharmaceutical composition of the present disclosure releases the active ingredient, in a nearly linear fashion, for at least about 2, 3, 4, 5, 6, 7, 8, 9, 10, 11, 12, 14, 16, 18, 20, 22, or 24 hours. A pharmaceutically active ingredient is released in a "nearly linear" fashion for a specified period of time if the release rate of the agent does not change more than 20% during each hour within the specified period of time.

In certain embodiments, the composition has the following in vitro dissolution rate measured by standard USP basket method provided herein: about 10% to about 60% of the active ingredient released after 4 hour; about 25% to about 75% of the active ingredient released after 8 hours, and about 30% to about 90% of the active ingredient released after 12 hours.

In certain embodiments, the composition has the following in vitro dissolution rate measured by the standard USP basket method provided herein: about 20% to about 50% of the active ingredient released after 4 hour; about 35% to about 65% of the active ingredient released after 8 hours, and about 40% to about 80% of the active ingredient released after 12 hours.

In certain embodiments, the composition has an in vitro dissolution rate measured by standard USP basket method provided herein of at most about 10%, 20%, 30%, 40%, 50%, 60%, 70%, 80%, or 90% of the active ingredient released after 2 hours, at most about 20%, 30%, 40%, 50%, 60%, 70%, 80%, or 90% of the active ingredient released after 4 hours, at most about 30%, 40%, 50%, 60%, 70%, 80%, or 90% of the active ingredient released after 6 hours, at most about 40%, 50%, 60%, 70%, 80%, or 90% of the active ingredient released after 8 hours, at most about 50%, 60%, 70%, 80%, or 90% of the active ingredient released after 10 hours, or at most about 60%, 70%, 80%, or 90% of the active ingredient released after 12 hours.

The term "initial burst" refers to uncontrolled dump or quick release of the active ingredient (e.g., greater than 10% of the drug load) from a dosage form immediately following an exposure to an aqueous medium (such as saliva or gastric fluid). A burst is undesired as it defeats the purpose of a sustained release and/or taste-masking for a chewable composition.

In certain embodiments, the compositions of the present disclosure have minimal initial burst of active ingredients, such as no greater than about 10%, 9%, 8%, 7%, 6%, 5%, 4%, 3%, 2% or 1% during the first 1 to 5 minutes in an in vitro dissolution assay (e.g., the standard USP basket method). Such a feature allows the making of taste-masking formulations, especially desirable for active ingredients with unpleasant tastes (e.g., tramadol, ibuprofen, cetaminophen, and certain vitamins) and for young human patients or for animal patients, such as cats.

In certain embodiments, the compositions of this disclosure are chewable. "Chewable," "chew resistant," or the like refers to the ability of a tablet or multiparticulate composition to maintain its sustained release property and taste-masking property if fragmented into 4 or more smaller pieces (e.g., 4 or more equal pieces).

In certain embodiments where the composition has the following in vitro dissolution rate measured by standard USP basket method provided herein: about 10% to about 60% of the active ingredient released after 4 hour; about 25% to about 75% of the active ingredient released after 8 hours, and about 30% to about 90% of the active ingredient released after 12 hours, the composition retains the above in vitro dissolution rate when the tablet or pellet is fragmented into 4 equal pieces.

In certain embodiments where the composition has the following in vitro dissolution rate measured by the standard USP basket method provided herein: about 20% to about 50% of the active ingredient released after 4 hour; about 35% to about 65% of the active ingredient released after 8 hours, and about 40% to about 80% of the active ingredient released after 12 hours, the composition retains the above in vitro dissolution rate when the tablet or pellet is fragmented into 4 equal pieces.

In certain embodiments, the average in vitro dissolution rate measured by standard USP basket method provided herein of a composition in tablet or multiparticulate forms (e.g., in a pellet form) during the first 2, 4, 6, 8, 10, or 12 hours does not increase by more than about 100%, 90%, 80%, 70%, 60%, 50%, 40%, 30%, 20% or 10% when the tablets or pellets are fragmented into 4 equal pieces.

In certain embodiments, the composition of the present disclosure, when administered orally to a patient in need thereof at the equivalent daily dose of an immediate release formulation, provides a plasma concentration of its active ingredient at or above its minimum effective concentration for a period of time at least about the same as, or about 1.5, 2, 3, 4, or 5 times of, that of the immediate release formulation administered at a daily standard dose (i.e., the daily dose according to the official product description for the formulation or the dose approved by a regulatory authority (e.g., the U.S. FDA) for the formulation).

F. Physical Form—Multiparticulates

In certain embodiments, the composition of the present disclosure is in the form of multiparticulates, discrete particles that make up a multiple-unit dosage form. Multiparticulates include, for example, pellets (e.g., spherical or non-spherical pellets) and granules.

The term "pellets" refers to small particles with approximately uniform shapes and sizes produced by an extrusion process. A "small particle" refers to a particle of which diameter, length, height, width, or the like is at most 10 mm (e.g., at most 2, 3, 4, 5, 6, 7, 8, or 9 mm). Small particles have approximately uniform sizes if the diameter, length, height, width, or the like of the smallest particle is at least about one half of the average diameter, length, height, width, or the like of the particles and if the diameter, length, height, width, or the like of the largest particle is at most about twice the average diameter, length, height, width, or the like of the particles.

In certain embodiments, the composition of the present disclosure is in the form of spherical pellets. The term "spherical pellet" refers to beads, beadlets, spherical particles, spheroids or the like that are of round or about round shape (i.e., having or approaching the shape of a small sphere) and are generally made by an extrusion and spheronization process.

In certain embodiments, the average size (i.e., the average diameter) of the spherical pellets according to this disclosure may be about 0.1 mm to about 3 mm, including any range formed by any two values between about 0.1 mm and about 3 mm.

In certain embodiments, the composition of the present disclosure may be in the form of non-spherical pellets (i.e., in the form other than spherical pellets), such as cylindrical pellets. In certain embodiments, the cylindrical pellets may a height from about the same to about 2-3 times of the cylinder diameter. In certain embodiments, the average cylinder diameter is about 0.1 mm to about 3 mm. The term "non-spherical pellet" also refers to extrudates or noodles, or noodlets are generally made by an extrusion process.

The term "granules" refers to small particles without approximately uniform shapes and sizes by a granulation process. Granules generally are less uniform in size or shape than pellets. In certain embodiments, the composition of the present disclosure may be in the form of granules.

G. Additional Ingredients and Coating

Optionally, the composition of the present disclosure (e.g., in the form of tablets) may comprise one or more pharmaceutically acceptable inactive ingredients, including binders, antioxidants, colorants, lubricants, glidants, and flavoring agents.

Suitable binders include water-soluble hydroxyalkyl celluloses such as povidone, polyvinylpyrrolidone, xanthan gum, cellulose gums such as hydroxypropyl cellulose, hydroxypropyl methylcellulose (HPMC), and sodium carboxymethylcellulose sodium (CMC), gelatin, starch, or water insoluble polymers, such as pre-gelatinized starch (e.g., STARCH 1500™ by Colorcon), acrylic polymers or copolymers, or alkyl celluloses such as ethyl cellulose.

Suitable antioxidants include butylated hydroxyanisole (BHA), butylated hydroxytoluene (BHT), vitamin E or ascorbyl palmitate.

Suitable colorants may be selected from any FD&C pigments, dyes or lakes.

Lubricants may also be incorporated into the composition of the present disclosure for a variety of reasons. They reduce friction between the powder and the die wall during compression and ejection. This prevents the powder from sticking to the tablet punches and facilitates its ejection from the tablet punches, etc. Examples of suitable lubricants include talc, stearic acid, vegetable oil, calcium stearate, zinc stearate, magnesium stearate, etc.

Glidants may also be incorporated into the compositions of the present disclosure. A glidant improves the flow characteristics of the powder. Examples of suitable glidants include talc, silicon dioxide, and cornstarch.

Other excipients that may be incorporated into the compositions of the present disclosure include preservatives or any other excipient commonly used in the pharmaceutical industry.

In certain embodiments, these other ingredients may be present in the tablets or multiparticulates at most about 50%, 40%, 30%, 20%, 10%, or 5% of the total weight of the tablets.

In certain embodiments, the composition of the present disclosure is optionally coated for additional drug release control, appearance, moisture protection or taste or flavor improvement.

The term "sustained release barrier coating" refers to a coating on a dosage form (e.g., tablets) that substantially slows the release of the active ingredient of the dosage form. More specifically, the presence of a sustained release barrier coating on a dosage form reduces the in vitro dissolution rate of the active ingredient within the first two hours (measured by the method disclosed herein) at least by about 50%.

Suitable sustained release coating materials include water-insoluble waxes, wax-like agents, and polymers such as hydrogenated vegetable oil (e.g., hydrogenated cottonseed oil), polymethacrylates (e.g., the EUDRAGIT™ polymers) or water insoluble celluloses, such as alkyl celluloses (e.g., ethylcellulose).

H. Exemplary Formulations

Unless otherwise provided, the exemplary formulations described in this subsection may comprise any active ingredient, especially one or more of those specifically described above, any primary sustained release agent (e.g., AQUA ZEIN®), any wax-like agent (e.g., hydrogenated vegetable oil and vegetable wax, especially hydrogenated cottonseed oil and carnauba wax), and any bulking or spheronizing agent (e.g., microcrystalline cellulose or a mixture of microcrystalline cellulose and pregelatinized starch). In addition, such exemplary formulations are in tablet or multi-particulate forms and provide sustained release of the active ingredient (e.g., having an in vitro dissolution rate of the active ingredient measured by the standard USP basket method of at most 90%, 80%, 70%, 60%, 50%, 40%, 30%, 20%, 10%, or 5% released after 2 hours, or meeting one or more of sustained release features provided herein, especially described in the above subsection entitled "E. Sustained Release") without requiring the presence of a sustained release barrier coating on the tablets or multiparticulates.

In certain embodiments, the multiparticulate composition of the present disclosure in a tablet or multiparticulate form comprises, consists essentially of, or consists of: (a) from about 1% to about 70% by weight of an active ingredient; (b) from 1% to 30% by weight of a primary sustained release agent; (c) from about 10% to about 80% by weight of a wax-like agent, and (d) from about 5% to about 70% by weight of a bulking or spheronizing agent In certain embodiments, the composition of the present disclosure in a tablet or multiparticulate form comprises, consists essentially of, or consists of: (a) from about 1% to about 30% by weight of an active ingredient; (b) from 1% to 20% by weight of a primary sustained release agent; (c) from about 5% to about 60% by weight of a wax-like agent, and (d) from about 5% to about 60% by weight of a bulking or spheronizing agent. In certain embodiments, the composition is in a tablet from and further comprises from about 10 to 50% tableting and/or coating ingredients.

In certain embodiments, the composition of the present disclosure in tablet or multiparticulate forms comprises, consists essentially of, or consists of: (a) from about 1% to about 80% by weight of an active ingredient; (b) from 1% to 30% by weight of a primary sustained release agent; (c) from about 1% to about 70% by weight of a wax-like agent, and (d) from about 5% to about 50% by weight of a bulking or spheronizing agent.

In certain embodiments, the composition of the present disclosure in tablet or multiparticulate forms comprises, consists essentially of, or consists of: (a) from about 3% to about 25% by weight of an active ingredient; (b) from 1% to 15% by weight of a primary sustained release agent; (c) from about 5% to about 55% by weight of a wax-like agent, and (d) from about 15% to about 45% by weight of a bulking or spheronizing agent.

In certain embodiments, the composition of the present disclosure in a tablet or multiparticulate form comprises, consists essentially of, or consists of: (a) from about 1% to about 80% by weight of an active ingredient; (b) from 1% to 30% by weight of zein from an aqueous dispersion of zein; (c) from about 1% to about 70% by weight of hydrogenated vegetable oil or vegetable wax, and (d) from about 5% to about 50% by weight of microcrystalline cellulose, pregelatinized starch or a mixture of microcrystalline cellulose and pregelatinized starch.

In certain embodiments, the composition of the present disclosure in a tablet or multiparticulate form comprises, consists essentially of, or consists of: (a) from about 3% to about 25% by weight of an active ingredient; (b) from 1% to 15% by weight of zein from an aqueous dispersion of zein; (c) from about 5% to about 55% by weight of hydrogenated vegetable oil or vegetable wax, and (d) from about 15% to about 45% by weight of microcrystalline cellulose, pregelatinized starch or a mixture of microcrystalline cellulose and pregelatinized starch.

In certain embodiments, the composition of the present disclosure in a tablet or multiparticulate form comprises, consists essentially of, or consists of: (a) from about 0.5% to about 20% by weight of phenylpropanolamine hydrochloride; (b) from 0.5% to 10% by weight of zein from an aqueous dispersion of zein; (c) from about 20% to about 80% by weight of hydrogenated vegetable oil or vegetable wax (e.g., hydrogenated cottonseed oil and carnauba wax), (d) from about 10% to about 40% by weight of microcrystalline cellulose, and (e) from about 5% to about 25% by weight of pregelatinized starch.

In certain embodiments, the composition of the present disclosure in a tablet or multiparticulate form comprises, consists essentially of, or consists of: (a) from about 1% to about 10% by weight of phenylpropanolamine hydrochloride; (b) from 1% to 5% by weight of zein from an aqueous dispersion of zein; (c) from about 40% to about 65% by weight of hydrogenated vegetable oil or vegetable oil (e.g., hydrogenated cottonseed oil and carnauba wax), (d) from about 15% to about 35% by weight of microcrystalline cellulose, and (e) from about 10% to about 20% by weight of pregelatinized starch.

In certain embodiments, the composition of the present disclosure in a tablet or multiparticulate form comprises, consists essentially of, or consists of: (a) from about 25% to about 75% by weight of glucosamine HCl, chondroitin, calcium ascorbate, manganese sulfate or a mixture thereof, (b) from about 1% to about 15% by weight of zein from an aqueous dispersion of zein, (c) from about 15% to about 35% by weight of hydrogenated vegetable oil or vegetable wax; (d) from about 5% to about 20% by weight of microcrystalline cellulose, and from about 5% to about 10% by weight of pregelatinized starch.

In certain embodiments, the composition of the present disclosure in a tablet or multiparticulate form comprises, consists essentially of, or consists of: (a) from about 1% to about 50% by weight of multi-vitamins and minerals, (b) from about 1% to about 20% by weight of zein from an aqueous dispersion of zein, (c) from about 1% to about 20% by weight of hydrogenated vegetable oil or vegetable wax (e.g., hydrogenated cottonseed oil or carnauba wax), and (d) from about 10% to about 50% by weight of microcrystalline cellulose.

In certain embodiments, the composition of the present disclosure in a tablet or multiparticulate form comprises, consists essentially of, or consists of: (a) from about 5% to about 30% by weight of tramadol HCl, (b) from about 1% to about 25% by weight of zein from an aqueous dispersion of zein, (c) from about 5% to about 50% by weight of hydrogenated vegetable oil or vegetable wax (e.g., hydrogenated cottonseed oil or carnauba wax), and (d) from about 15% to about 60% by weight of microcrystalline cellulose.

In certain embodiments, the composition of the present disclosure in a tablet or multiparticulate form comprises, consists essentially of, or consists of: (a) about 4% or 5% by weight of phenylpropanolamine hydrochloride; (b) about 2.5% by weight of zein from an aqueous dispersion of zein; (c) about 50% by weight of hydrogenated vegetable oil or vegetable wax (e.g., hydrogenated cottonseed oil and carnauba wax), (d) about 24% by weight of microcrystalline cellulose, and (e) about 14% by weight of pregelatinized starch.

In certain embodiments, the composition of the present disclosure in a tablet or multiparticulate form comprises, consists essentially of, or consists of: (a) about 4% by weight of phenylpropanolamine hydrochloride; (b) about 5% by weight of zein from an aqueous dispersion of zein; (c) about 48% by weight of hydrogenated vegetable oil or vegetable wax (e.g., hydrogenated cottonseed oil and carnauba wax), (d) about 24% by weight of microcrystalline cellulose, and (e) about 14% by weight of pregelatinized starch.

In certain embodiments, the composition of the present disclosure in a tablet or multiparticulate form comprises, consists essentially of, or consists of: (a) about 1% by weight of phenylpropanolamine hydrochloride; (b) about 2.5% by weight of zein from an aqueous dispersion of zein; (c) about 49% by weight of hydrogenated vegetable oil or vegetable wax (e.g., hydrogenated cottonseed oil and carnauba wax), (d) about 27% by weight of microcrystalline cellulose, and (e) about 14% by weight of pregelatinized starch.

In certain embodiments, the composition of the present disclosure in a tablet or multiparticulate form comprises, consists essentially of, or consists of: (a) about 22.50% by weight of glucosamine HCl, about 10.10% chondroitin sulfate, about 1.12% calcium ascorbate, and about 0.28% manganese sulfate; (b) about 10.20% by weight of zein from an aqueous dispersion of zein; (c) about 27.43% by weight of hydrogenated vegetable oil or vegetable wax (e.g., hydrogenated cottonseed oil and carnauba wax), (d) about 14.69% by weight of microcrystalline cellulose, and (e) about 7.68% by weight of pregelatinized starch.

In certain embodiments, the composition of the present disclosure in a tablet or multiparticulate form comprises, consists essentially of, or consists of: (a) about 15% to about 30% by weight of glucosamine HCl, about 5% to about 15% chondroitin sulfate, about 0.5% to about 2% calcium ascorbate, and about 0.1% to about 0.5% manganese sulfate; (b) about 5% to about 15% by weight of zein from an aqueous dispersion of zein; (c) about 20% to about 35% by weight of hydrogenated vegetable oil or vegetable wax (e.g., hydrogenated cottonseed oil and carnauba wax), (d) about 10% to about 20% by weight of microcrystalline cellulose, and (e) about 5% to about 10% by weight of pregelatinized starch.

In certain embodiments, the composition of the present disclosure in a tablet or multiparticulate form comprises, consists essentially of, or consists of: (a) about 63.7% by weight of glucosamine HCl; (b) about 2% by weight of zein from an aqueous dispersion of zein; (c) about 20% by weight of hydrogenated vegetable oil or vegetable wax (e.g., hydrogenated cottonseed oil and carnauba wax), (d) about 8.8% by weight of microcrystalline cellulose, and (e) about 5.9% by weight of pregelatinized starch.

In certain embodiments, the composition of the present disclosure in a tablet or multiparticulate form comprises, consists essentially of, or consists of: (a) about 60% to about 70% by weight of glucosamine HCl; (b) about 1% to about 2% by weight of zein from an aqueous dispersion of zein; (c) about 15% to about 25% by weight of hydrogenated vegetable oil or vegetable wax (e.g., hydrogenated cottonseed oil and carnauba wax), (d) about 5% to about 15% by weight of microcrystalline cellulose, and (e) about 3% to about 10% by weight of pregelatinized starch.

In certain embodiments, the composition of the present disclosure in a tablet or multiparticulate form comprises, consists essentially of, or consists of: (a) about 28% by weight of glucosamine HCl; (b) about 2% by weight of zein from an aqueous dispersion of zein; (c) about 20% by weight of hydrogenated vegetable oil or vegetable wax (e.g., hydrogenated cottonseed oil and carnauba wax), (d) about 8.8% by weight of microcrystalline cellulose, and (e) about 5.9% by weight of pregelatinized starch.

In certain embodiments, the composition of the present disclosure in a tablet or multiparticulate form comprises, consists essentially of, or consists of: (a) about 20% to about 35% by weight of glucosamine HCl; (b) about 1% to about 5% by weight of zein from an aqueous dispersion of zein; (c) about 15% to about 25% by weight of hydrogenated vegetable oil or vegetable wax (e.g., hydrogenated cottonseed oil and carnauba wax), (d) about 5% to about 15% by weight of microcrystalline cellulose, and (e) about 3% to about 10% by weight of pregelatinized starch.

In certain embodiments, the composition of the present disclosure in a tablet or multiparticulate form comprises, consists essentially of, or consists of: (a) about 70% by weight of multi-vitamins and minerals; (b) about 4% by weight of zein from an aqueous dispersion of zein; (c) about 6.4% by weight of carnauba wax or hydrogenated cottonseed oil, and (d) about 15% by weight of microcrystalline cellulose.

In certain embodiments, the composition of the present disclosure in a tablet or multiparticulate form comprises, consists essentially of, or consists of: (a) about 60% to about 80% by weight of multi-vitamins and minerals; (b) about 1% to about 15% by weight of zein from an aqueous dispersion of zein; (c) about 3% to about 25% by weight of hydrogenated vegetable oil or vegetable wax (e.g., hydrogenated cottonseed oil and carnauba wax), and (d) about 10% to about 60% by weight of microcrystalline cellulose.

In certain embodiments, the composition of the present disclosure in the form of coated tablets or multiparticulates comprises, consists essentially of, or consists of: (a) about 10% by weight of tramadol HCl; (b) about 5% by weight of zein from an aqueous dispersion of zein; (c) about 50% by weight of hydrogenated vegetable oil or vegetable wax (e.g., hydrogenated cottonseed oil and carnauba wax), wherein about 45.2% of the hydrogenated vegetable oil or vegetable wax is present as a coating on the tablets or multiparticulates, and about 4.8% of the hydrogenated vegetable oil or vegetable wax is present in the core of the tablets or multiparticulates, (d) about 27.75% by weight of microcrystalline cellulose, and (e) about 2.5% by weight of pregelatinized starch. In certain embodiments, the coated tablets or multiparticulates further comprise about 4.8% of a flavorant (e.g., pork liver flavor or tuna flavor) in the coating.

In certain embodiments, the composition of the present disclosure in the form of coated tablets or multiparticulates comprises, consists essentially of, or consists of: (a) about 5% to about 15% by weight of tramadol HCl; (b) about 1% to about 10% by weight of zein from an aqueous dispersion of zein; (c) about 40% to about 60% by weight of hydrogenated vegetable oil or vegetable wax (e.g., hydrogenated cottonseed oil and carnauba wax), wherein 35% to about 55% of the hydrogenated vegetable oil or vegetable wax is present as a coating on the tablets or multiparticulates, and about 3% to about 6% of the hydrogenated vegetable oil is present in the core of the tablets or multiparticulates (d) about 20% to about 35% by weight of microcrystalline cellulose, and (e) about 1% to about 5% by weight of pregelatinized starch. In certain embodiments, the coated tablets or multiparticulates further comprise about 3% to about 10% of a flavorant (e.g., pork liver flavor or tuna flavor) in the coating.

In certain embodiments, the composition of the present disclosure in the form of coated tablets or multiparticulates comprises, consists essentially of, or consists of: (1) in the core, (a) about 20.5% by weight of tramadol HCl; (b) about 25.5% by weight of zein from an aqueous dispersion of zein; (c) about 30.9% by weight of carnauba wax, and (d) about 23.1% by weight of microcrystalline cellulose; and (2) in the coating, hydrogenated vegetable oil (e.g., hydrogenated cottonseed oil), wherein the coating is about 40% by weight of the coated tablets or multiparticulates.

In certain embodiments, the composition of the present disclosure in the form of coated tablets or multiparticulates comprises, consists essentially of, or consists of: (1) in the core, (a) about 10% to about 30% by weight of tramadol HCl; (b) about 20% to about 30% by weight of zein from an aqueous dispersion of zein; (c) about 20% to about 40% by weight of hydrogenated vegetable oil or vegetable wax (e.g., hydrogenated cottonseed oil and carnauba wax), and (d) about 20% to about 30% by weight of microcrystalline cellulose; and (2) in the coating, hydrogenated vegetable oil (e.g., hydrogenated cottonseed oil), wherein the coating is about 30% to about 50% by weight of the coated tablets or multiparticulates.

II. Dosage Forms

In another aspect, oral dosage forms that comprise the compositions disclosed herein are provided.

The term "oral dosage form" refers to a device that collectively delivers, by oral ingestion, the desired amount of an active ingredient, to achieve a desired dose of the active ingredient. Typically, the oral dosage form is a powder for oral suspension, a unit dose packet or sachet, a tablet, or a capsule.

In certain embodiments, the pellets of the present disclosure may be mixed with a vehicle and packaged in a container such as a screw cap bottle. Prior to dosing, the mixture is added with water or another liquid and shaken to form an "oral suspension." In this oral suspension, the pellets containing the active ingredient may be (a) completely suspended in the vehicle, or (b) partially suspended in the vehicle and partially in solution with the vehicle.

In certain embodiments, the multiparticulate composition of the present disclosure may be mixed with or placed on feed to allow the animal patient to eat voluntarily.

The term "vehicle" refers to a mixture of pharmaceutically acceptable ingredients put together to facilitate the suspension of pellets and improve the taste of an oral suspension. A vehicle useful in this invention may contain suspending agents, anticaking agents, fillers, sweeteners, flavorants, colorants, and/or lubricants.

Examples of suspending agents or thickeners include xanthan gum, starch, guar gum, sodium alginate, carboxymethyl cellulose, sodium carboxymethyl cellulose, methyl cellulose, hydroxypropyl methyl cellulose, polyacrylic acid, silica gel, aluminum silicate, magnesium silicate, and titanium dioxide.

Examples of anticaking agents or fillers include colloidal silicon oxide and lactose.

Other conventional excipients may be employed in the compositions of this invention, including those excipients well-known in the art. Generally, excipients such as pigments, lubricants, sweeteners, flavorants, and so forth may be used for customary purposes and in typical amounts without adversely affecting the properties of the compositions.

In certain embodiments, the dosage form may be packaged in a bottle, packet, pouch, sachet, or capsule.

In certain embodiments, the dosage form comprises the active ingredient at a dose of at least about 10, 20, 50, 100, 200, 250, 300, 400, 500, 600, 700, 750, 800, or 900 mg, or about 1, 2, 3, 4, 5, 6, 7, 8, 9, or 10 gram per dose.

In certain embodiments, the present disclosure provides unitary dosage forms that comprise an effective amount of phenylpropanolamine hydrochloride. In certain embodiments, such dosage forms may contain from about 25 mg to about 150 mg phenylpropanolamine hydrochloride per unit, such as from about 50 mg to about 100 mg of phenylpropanolamine hydrochloride per unit, or about 75 mg per unit.

In certain embodiments, the dosage form is for single dose use. "Single dose," as used herein, refers to administering only one dose of an active ingredient in the full course of therapy.

In certain embodiments, the dosage form, upon oral administration to a patient in need thereof, provides a plasma concentration of the active agent in the patient at or above its minimum effective concentration for at least about 2, 4, 6, 8, 10, 12, 14, 16, 18, 20, 24, 36, 48, 72, 96, 120, 144, or 168 hours.

In certain embodiments, the dosage form, upon oral administration to a patient in need thereof, provides a plasma concentration of the active agent in the patient at or above its minimum effective concentration for a period of time that is at least about 2, 3, 4, or 5 times of that of an immediate release formulation administered at a standard dose.

In certain embodiments, the dosage form is suitable for administration to a patient in need thereof at, or no more than, once or twice per day, once per two, three, four, five, six, seven days, once per one, two, three, or four weeks, or once per treatment.

III. Methods of Making Compositions

In another aspect, the present disclosure provides a method for making the compositions and dosage forms described herein.

For example, in one aspect, the present disclosure provides a method for making the chewable, sustained release multiparticulate composition comprising (i) an active ingredient; (ii) a primary sustained release agent, (iii) a wax-like agent; and (iv) a bulking or spheronizing agent, the method comprising: (a) mixing the active ingredient with the primary sustained release agent to form a core; (b) mixing the core of step (a) with the wax-like agent, the bulking or spheronizing agent, and a liquid (e.g., water or a pharmaceutical solvent); (c) granulating or extruding the mixture of step (b) to obtain granules or extrudates, (d) drying the granules or extrudates, (e) heating the dry granules or extrudates to a temperature exceeding the melting point of the wax-like agent, and (f) sizing the dry granules or fragmenting the dry extrudates to form non-spherical pellets.

In certain embodiments, (i) an active ingredient; (ii) a primary sustained release agent, (iii) a wax-like agent; and (iv) a bulking or spheronizing agent, the method comprising: (a) mixing the active ingredient with the primary sustained release agent to form a core, (b) mixing the core with the wax-like agent, the bulking or spheronizing agent, and a liquid (e.g., water or a pharmaceutical solvent); (c) extruding to obtain extrudate, (d) spheronizing the extrudates to form spherical pellets, (e) drying the spherical pellets, and (f) heating the dry pellets to a temperature exceeding the melting point of the wax-like agent.

In certain embodiments, the dry granules, non-spherical pellets, or spherical pellets are further filled into capsules.

In certain embodiments, the dry granules, non-spherical pellets, or spherical pellets are further coated with a coating composition provided herein, such as a coating composition that comprises a wax-like agent.

In certain embodiments, the dry granules, non-spherical pellets, or spherical pellets were further mixed with other tableting ingredients and compressed into tablets. In certain embodiments, the tablets are further coated with a coating composition provided herein, such as a coating composition that comprises a wax-like agent.

The wet granules, extrudates or spherical pellets or non-spherical pellets made from above processes may be dried and heated at a temperature exceeding the melting point of the wax-like agent. The drying/heating process may be applied in two consecutive steps. The first stage of drying is primarily to remove water and to cause the granules/extrudates/pellets to sufficiently harden to allow for more rigorous heating in the second stage of heating. A lower temperature (e.g., about 40° C., which is below the melting point of the wax-like agent, or ambient temperature, i.e., about 20° C. to about 25° C.) is usually sufficient for the drying purpose and is preferred for the stability of the active ingredient. The drying time of the first stage may vary from 10 minutes to several hours or longer depending upon the batch size, efficiency of the dryer used, and the drying temperature. The end point for the first stage of drying is water content (i.e., moisture level) of no more than about 10% relative to the total weight of the granules, extrudate, or pellets after the first stage of drying.

The second stage of drying further reduces the water content to no more than about 5% (e.g., no more than about 2%). In certain embodiments, the second stage of drying is performed at a temperature about 10° C. to about 20° C. higher than the melting point of the wax-like agent (e.g., at about 60° C. to about 75° C.) to remove the tightly bound water. The drying time of the second stage drying may vary, such as from 15 minutes to several hours or longer depending upon the batch size and efficiency of the dryer. An even higher temperature may be applied so long that it does not cause deformation or agglomeration of the granules/extrudates/pellets or thermal degradation of the active or other ingredients. In addition to lowering the water content to no more than about 5%, the second stage is to provide additional sustained release and taste-masking property.

Not wishing to be bound by any theory, the second stage of drying, which resembles a thermal annealing treatment, is believed to cause a partial melting of the wax-like agent and to seal any cracks, pores or crevasses that may present in the dry multiparticulate composition (i.e. granules, extrudates, spherical pellets, or non-spherical pellets).

In certain embodiments, the drying process is one continuous step where the temperature is ramped from about room temperature to about 10° C. to about 20° C. above the melting point of the wax-like agent in a timed program. In certain embodiments, the drying and heating of granules, extrudates, spherical pellets, or non-spherical pellets may be performed in a fluid bed process, convection or microwave oven.

In certain embodiments, the drying process comprises a third step of further drying the granules, extrudate, spherical pellets, or non-spherical pellets at a temperature below the melting point of the wax-like agent until the moisture level of the resulting extrudate is no more than 1%. This third drying step may be a distinct step or may be combined with the first and second drying steps into one continuous step.

Although drying at a temperature higher than the melting temperature of the wax-like agent is preferred in certain embodiments, it is not required. Accordingly, in certain other embodiments, the wet granules, extrudate, spherical pellets, or non-spherical pellets may be dried only at a temperature below the melting temperature of the wax-like agent.

In certain embodiments, the dry granules, spherical or non-spherical pellets or tablets produced via the above extrusion process are further coated with a coating composition. Such a coating composition may comprise a wax-like agent, a primary sustained release agent, a flavorant, a colorant or a combination thereof.

IV. Methods of Using Compositions and Dosage Forms

In one aspect, the present disclosure provides methods for using the pharmaceutical compositions and dosage forms described herein. Such pharmaceutical compositions and dosage forms may be used for treating or preventing (i.e., reducing the risk of) diseases or disorders that the pharmaceutically active agents in the compositions are suitable for treating or preventing.

The diseases or disorders include, but are not limited to, incontinence, congestion, hypothyroidism, hyperthyroidism, anxiety, depression and other behavioral disorders, pain, inflammation, infection, diabetes, hyperphosphataemia, chronic diseases, and dietary deficiencies.

In certain embodiments, the present disclosure provides a method for treating incontinence in an animal, comprising administering orally to an animal patient in need thereof a pharmaceutical composition or dosage form as described herein that comprises an effective amount of phenylpropanolamine or its pharmaceutically acceptable salt (e.g., phenylpropanolamine hydrochloride).

In certain embodiments, the present disclosure provides a method for treating congestion, comprising administering orally to a patient in need thereof a pharmaceutical composition or dosage form as described herein that comprises an effective amount of phenylpropanolamine or its pharmaceutically acceptable salt (e.g., phenylpropanolamine hydrochloride).

In certain embodiments, the present disclosure provides a method for suppressing appetite, comprising administering orally to a patient in need thereof a pharmaceutical composition or dosage form as described herein that comprises an effective amount of phenylpropanolamine or its pharmaceutically acceptable salt (e.g., phenylpropanolamine hydrochloride).

In certain embodiments, the present disclosure provides a method for treating hypothyroidism, comprising administering orally to a patient in need thereof a pharmaceutical composition or dosage form as described herein that comprises an effective amount of levothyroxine sodium.

In certain embodiments, the present disclosure provides a method for treating hyperthyroidism, comprising administering orally to a patient in need thereof a pharmaceutical composition or dosage form as described herein that comprises an effective amount of methimazole.

In certain embodiments, the present disclosure provides a method for treating anxiety, depression or another behavioral disorder, comprising administering orally to a patient in need thereof a pharmaceutical composition or dosage form as described herein that comprises an effective amount of an anti-anxiety agent, antidepressant or a behavior modifying drug. In certain embodiments, the anti-anxiety agent, antidepressant, or behavior modifying drug is buspirone hydrochloride, fluoxetine hydrochloride, paroxetine, amitriptyline hydrochloride, clomipramine hydrochloride, doxepin, or imiproamine hydrochloride.

In certain embodiments, the present disclosure provides a method for reducing pain, comprising administering orally to a patient in need thereof a pharmaceutical composition or dosage form as described herein that comprises an effective amount of tramadol or a pharmaceutically acceptable salt.

In certain embodiments, the present disclosure provides a method for treating inflammation, comprising administering orally to a patient in need thereof a pharmaceutical composition or dosage form as described herein that comprises an effective amount of a nonsteroidal anti-inflammatory drug. In certain embodiments, the nonsteroidal anti-inflammatory drug is carprofen, deracoxib, etodolac, firocoxib, ketoprofen, meloxicam, piroxicam, or tepoxalin.

In certain embodiments, the present disclosure provides a method for treating diabetes, comprising administering orally to a patient in need thereof a pharmaceutical composition or dosage form as described herein that comprises an effective amount of an anti-diabetic agent. In certain embodiments, the anti-diabetic agent is glipizide, metformin hydrochloride, acarbose, or glibenclamide.

In certain embodiments, the present disclosure provides a method for treating hyperphosphataemia, comprising administering orally to a patient in need thereof a pharmaceutical composition or dosage form as described herein that comprises an effective amount of a phosphate binding compound. In certain embodiments, the phosphate binding compound is sevelamer hydrochloride, aluminum carbonate, or aluminum hydroxide.

In certain embodiments, the present disclosure provides a method for treating or preventing a chronic disease, comprising administering orally to a patient in need thereof a pharmaceutical composition or dosage form as described herein that comprises an effective amount of nutraceutical. In certain embodiments, the nutraceutical is glucosamine hydrochloride, chondroitin sulfate, a vitamin, a milk protein concentrate, an anti-oxidant, an anti-inflammatory agent, a flavonoid, a prebiotic, a weight loss agent, multi-vitamins, or minerals.

In certain embodiments, the present disclosure provides a method for treating or preventing a dietary deficiency, comprising administering orally to a patient in need thereof a pharmaceutical composition or dosage form as described herein that comprises an effective amount of nutraceutical. In certain embodiments, the nutraceutical is glucosamine hydrochloride, chondroitin sulfate, a vitamin or multi-vitamins, minerals, a milk protein concentrate, an anti-oxidant, an anti-inflammatory agent, a flavonoid, a prebiotic, a weight loss agent, or a combination thereof.

Patients in need of treatment or prevention of a disease or disorder include both human patients (e.g., adult human patients) and non-human patients (e.g., dogs, cats, horses, and other pets or farm animals).

An "effective amount" refers to the amount of a pharmaceutically active agent effective in treating or preventing a disease or disorder. Such amount may be determined by appropriate methods known in the art. For instance, a sufficient amount of an analgesic or analgesics (such as tramadol and acetaminophen) in a pharmaceutical composition of the present disclosure may be determined using various methods for measuring analgesia, such as those described in U.S. Patent Application Publication No. 20050089558, Collier et al., Br. J. Pharmacol. 32: 295, 1968; D'Amour et al., J. Pharmacol. Exp. Ther. 72: 74, 1941; and Hargreaves et al., Pain 32: 77, 1988.

The following example is provided by way of illustration, and not by way of limitation.

EXAMPLES

Example 1

Preparing Phenylpropanolamine (PPA) Chewable Sustained Release Tablets Via Extrusion Chewable sustained release tablets each containing 75 mg phenylpropanolamine (PPA) were made according to the method described below. The in vitro dissolution profiles of said chewable tablets were compared to those of the marketed product, CYSTOLAMINE® capsules (also containing 75 mg PPA per capsule).

Materials:

TABLE 1A

| Ingredient | Supplier |
|---|---|
| Phenylpropanolamine HCl | Spectrum Chemicals |
| Microcrystalline Cellulose (Avicel PH102) | FMC Biopolymer |
| Pregelatinized Starch (Starch 1500) | Colorcon |
| Hydrogenated Cottonseed Oil | Stereotex |
| AQUA ZEIN ® w/ Ammonia (14% Zein) | Freeman Industries |
| Deionized Water | LATITUDE Pharmaceuticals |

Compositions:

Study 1—Experimental Formulation

A. Noodle-Shape Extrudates ("Noodles") Containing 2.5% Zein

TABLE 1B

| Ingredient | Batch Wt. (g) | | % (w/w in dry wt) |
|---|---|---|---|
| | Wet Mass | Dry Mass | |
| Phenylpropanolamine HCl | 12.0 | 12.0 | 4.0 |
| Microcrystalline Cellulose | 75.0 | 75.0 | 25.0 |
| Pregelatinized Starch | 45.0 | 45.0 | 15.0 |
| Hydrogenated Cottonseed Oil | 160.5 | 160.5 | 53.5 |
| AQUA ZEIN ® (14% in water) | 53.6 | 7.5 | 2.5 |
| D.I. Water | 160.0 | 0.0 | 0.0 |
| Total | 506.1 | 300.0 | 100.0 |

B. Noodles Containing 5% Zein

TABLE 1C

| Ingredient | Batch Wt. (g) | | % (w/w in dry wt) |
|---|---|---|---|
| | Wet Mass | Dry Mass | |
| Phenylpropanolamine HCl | 12.0 | 12.0 | 4.0 |
| Microcrystalline Cellulose | 75.0 | 75.0 | 25.0 |
| Pregelatinized Starch | 45.0 | 45.0 | 15.0 |
| Hydrogenated Cottonseed Oil | 153.0 | 153.0 | 51.0 |
| AQUA ZEIN ® (14% in water) | 107.1 | 15.0 | 5.0 |
| D.I. Water | 120.0 | 0.0 | 0.0 |
| Total | 512.1 | 300.0 | 100.0 |

C. Tablet

TABLE 1D

| Ingredient | Batch Wt. (g) | Unit Wt. (mg) | % (w/w) |
|---|---|---|---|
| "Noodles" from Table 1B or 1C | 94.0 | 1880.0 | 94.0 |
| Pork Liver Flavor | 5.0 | 100.0 | 5.0 |
| Magnesium Stearate | 1.0 | 19.7 | 1.0 |
| Total Target Weight | 100.0 | 2000.0 | 100.0 |

Study 2—Prototype Formulation

A. Noodles with 2.5% AQUA ZEIN®

TABLE 1E

| Ingredient | Batch Wt. (g) | | % (w/w in dry wt) |
|---|---|---|---|
| | Wet Mass | Dry Mass | |
| Phenylpropanolamine HCl | 15.0 | 15.0 | 5.0 |
| Microcrystalline Cellulose | 75.0 | 75.0 | 25.0 |
| Pregelatinized Starch | 45.0 | 45.0 | 15.0 |
| Hydrogenated Cottonseed Oil | 157.5 | 157.5 | 52.5 |
| AQUA ZEIN ® (14% in water) | 53.6 | 7.5 | 2.5 |
| D.I. Water | 160.0 | 0.0 | 0.0 |
| Total | 506.1 | 300.0 | 100.0 |

B. Tablet

TABLE 1F

| Ingredient | Batch Wt. (g) | Unit Wt. (mg) | % (w/w) |
|---|---|---|---|
| Noodles from Table 1E | 141.0 | 1852.0* | 94.0 |
| Pork Liver Flavor | 7.5 | 98.5 | 5.0 |
| Magnesium Stearate | 1.5 | 19.7 | 1.0 |
| Total Target Weight | 150.0 | 1970.2 | 100.0 |

*Containing 75 mg Phenylpropanolamine (PPA) as free base

Manufacturing Procedure:

Noodles:

AQUA ZEIN® was mixed with PPA using a low-shear mixer prior to blending with Avicel PH102, starch and cottonseed oil. Water was added to produce a wet-mass material (dough) targeting moisture content at about 40%. Extrudates (wet noodles) were produced by passing the dough through 1.2 mm dome screen of an extruder. The wet noodles were dried under ambient temperature for over night prior to heating in an oven at 60-70° C. until the moisture level is ≤5%. The noodles were continued to dry using a fluid bed dryer until the moisture level is ≤1%.

Tablets:

The dried noodles were fragmented and forcing through a 10-mesh screen sieve. The sized noodles were mixed with a 5% pork liver flavor using a V-blender prior to lubricating with 1% magnesium stearate. Tablets were compressed to the target weight with the hardness >20 Kp.

Analytical Testing:

HPLC Assay:

The analysis of PPA potency in the tablet or noodle samples was performed using a RP-HPLC method under the following operating conditions:

TABLE 1G

| HPLC system: | Shimadzu (LC-10AD) | |
|---|---|---|
| Column: | Thermo-Bata Basic 18, 150 × 4.6 mm, 5 μ | |
| Column Temp: | 30° C. | |
| Mobile Phase A: | 0.041% w/v triethylamine, 0.015% w/v phosphoric acid, 0.48% w/v monobasic sodium phosphate, 0.152% w/v sodium 1-hexamesulfonate, 20% v/v methanol in water | |
| Mobile Phase B: | 100% Methanol | |
| | Time (min) | % Mobile Phase B |
| Gradient: | 0.0 | 30 |
| | 4.0 | 100 |
| | 6.0 | 100 |
| | 6.5 | 30 |
| | 10.0 | 30 |
| Detector: | UV | |
| Wavelength | 210 nm | |
| Injection volume: | 20 μL | |
| Flow Rate: | 1.0 mL/min | |
| Run Time: | 10 min | |
| Sample concentration | 1.0 mg/mL | |

In Vitro Dissolution:

The chewable sustained release tablets were tested for in vitro dissolution using USP dissolution apparatus under the conditions as follows:

TABLE 1H

| Apparatus | USP dissolution apparatus I (basket) |
|---|---|
| Medium | Water |
| Medium volume | 1000 mL |
| Temperature | 37° C. |

TABLE 1H-continued

| | |
|---|---|
| Stirring speed | 50 RPM |
| Sample volume | 1 mL (without replenishment with fresh medium). Each sample was filtered through a 30-micron filter prior to filling into HPLC vial. |
| Testing instrument | HPLC |

Results:

The in vitro dissolution profiles of chewable sustained release tablets (n=2 each) containing 75 mg strength of PPA as hydrochloride salt at various levels of Zein were presented in FIG. 1. The profiles of 4 pieces cut tablets were also included to simulate the chewed tablets. The tablets containing 2.5% Zein for both intact and 4 pieces cut tablets demonstrated slower dissolution rates than that containing 5% Zein. Both formulations completely released PPA within 24 hours. The marketed product, CYSTOLAMINE®, on the other hand, completely released PPA within the first 12 hours.

Example 2

Preparing Phenylpropanolamine (PPA) Chewable Sustained Release Tablets Via Wet Granulation Chewable sustained release tablets containing phenylpropanolamine HCL (e.g., 5% w/w) may be prepared via a high shear wet granulation process.

Composition:

TABLE 2A

| | F-26 10 mg | F-25 20 mg | F-29 50 mg | F-22-2 75 mg |
|---|---|---|---|---|
| Ingredient, % wt | | | | |
| Phenylpropanolamine HCl | 1.24 | 1.24 | 4.70 | 4.70 |
| Microcrystalline Cellulose | 26.96 | 26.96 | 23.50 | 23.50 |
| Pregelatinized Starch | 14.10 | 14.10 | 14.10 | 14.10 |
| Hydrogenated Cottonseed Oil | 49.35 | 49.35 | 49.35 | 49.35 |
| Zein (from AQUA ZEIN ®) | 2.35 | 2.35 | 2.35 | 2.35 |
| Pork Liver Flavor | 5.00 | 5.00 | 5.00 | 5.00 |
| Magnesium Stearate | 1.00 | 1.00 | 1.00 | 1.00 |
| Total | 100.00 | 100.00 | 100.00 | 100.00 |
| Ingredient, mg/tablet | | | | |
| Phenylpropanolamine HCl | 12.4 | 24.8 | 62.7 | 92.6 |
| Microcrystalline Cellulose | 269.6 | 539.2 | 313.3 | 463.0 |
| Pregelatinized Starch | 141.0 | 282.0 | 188.0 | 277.8 |
| Hydrogenated Cottonseed Oil | 493.5 | 987.0 | 658.0 | 972.3 |
| Zein (from AQUA ZEIN ®) | 23.5 | 47.0 | 31.3 | 46.3 |
| Pork Liver Flavor | 50.0 | 100.0 | 66.7 | 98.5 |
| Magnesium Stearate | 10.0 | 20.0 | 13.3 | 19.7 |
| Total | 1000 | 2000 | 1333.3 | 1970.2 |

Figure 15A:
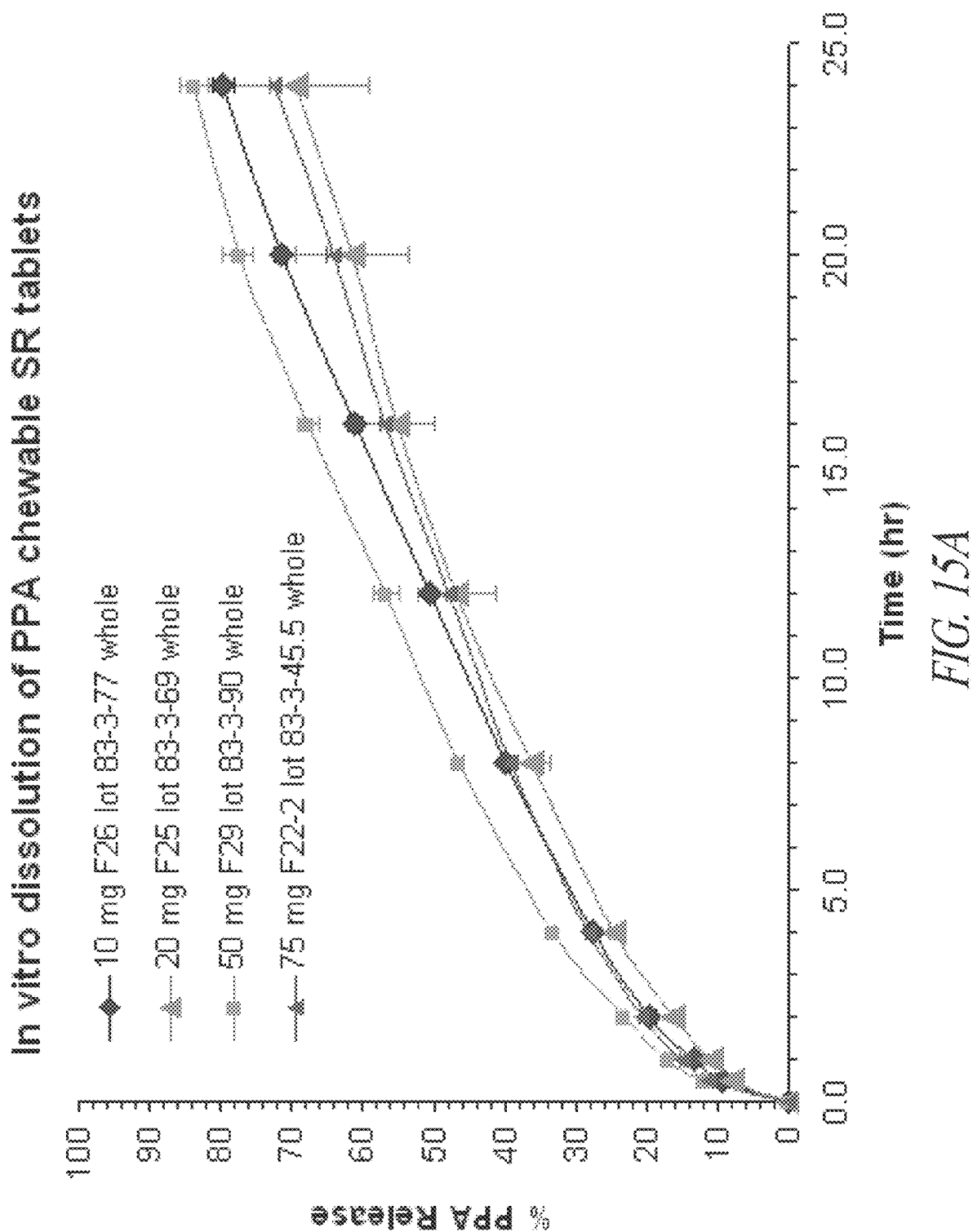
FIGS. 15A and 15B. In vitro dissolution profiles of 10, 20, 50 and 75 mg phenylpropanolamine (PPA) HCl sustained release tablets, as whole tablets (A) and quartered tablets (B).
Figure 15B:
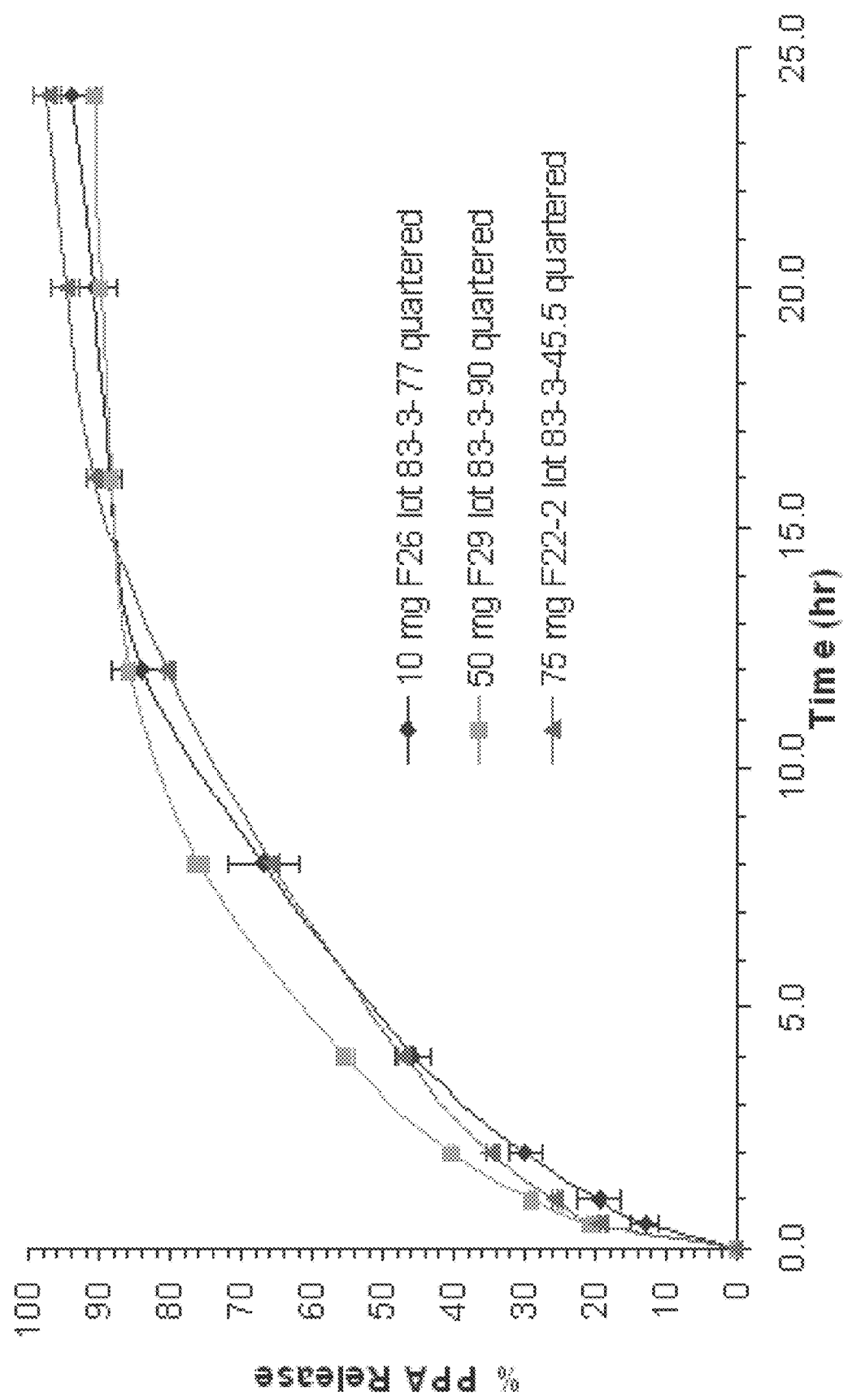

Manufacturing Process:
Wet Granulation:
1. Dissolve PPA hydrochloride in AQUA ZEIN® in a low-shear mixing bowl.
2. Blend microcrystalline cellulose, pregelatinized starch and hydrogenated cottonseed oil using a V-blender for 10 minutes.
3. Add the blend into the mixing bowl.
4. While mixing, gradually add water to produce wet granules with about 40% moisture content.
5. Size the wet granules by passing through a sieve of No. 14 mesh.
6. Air-dry the sized granules at ambient temperature over night.
7. Further dry in an oven at 60-70° C. until moisture level is <5%.
8. Continue to dry using a fluid bed dryer until the moisture level is <1%.
9. Pass dried granules through a 10-mesh sieve to de-lump.
10. Transfer the sized dry granules to a V-blender, add pork liver flavor, and then mix for 5 minutes.
11. Add magnesium stearate and then mix for 3 minutes.
12. Compress the final blend into tablets to the target weight with hardness of >20 Kp Results:

In vitro dissolution profiles of the 10 mg, 20 mg, 50 mg and 75 mg tablets were comparable to each other, as in whole tablets or quartered ones (FIGS. 15A and 15B). They provided an extended release profile (≥24 hr) as a whole tablet or sustained release profile (≥12 hr) after being cut into 4 parts.

Example 3

Chewable and Sustained Release Tablet Formulation Containing Glucosamine HCl, Chondroitin Sulfate, Calcium Ascorbate and Manganese Sulfate This study was to develop a chewable sustained release tablet formulation that contains glucosamine HCl, chondroitin, ESTER-C® and Manganese Sulfate. The tablet was 2 g in weight and round in shape, containing glucosamine HCl, chondroitin, ESTER-C® and manganese sulfate, and is suitable for administering to animals, such as dogs. ESTER-C® contains mainly calcium ascorbate, small amounts of the vitamin C metabolites dehydroascorbate (oxidized ascorbic acid), calcium threonate, and trace levels of xylonate and lyxonate. A wet granulation process was developed using low shear granulation. AQUA ZEIN® and hydrogenated cottonseed oil were used. This uncoated non-disintegrating tablet releases glucosamine in about 24 hours as a whole tablet, and about 12 hours as quartered tablet. Pork liver flavor was included to increase canine acceptance.

Composition:

TABLE 3A

| Ingredient | % (w/w) | mg/tablet |
|---|---|---|
| Glucosamine HCl | 22.50 | 450.0 |
| Chondroitin sulfate, ESTER-C ®, Manganese Sulfate | 11.5 | 230 |
| Microcrystalline Cellulose | 14.69 | 293.8 |
| Pregelatinized Starch | 7.68 | 153.6 |
| Hydrogenated Cottonseed Oil | 27.43 | 548.6 |
| Zein (total zein from AQUA ZEIN ® and dry zein) | 10.20 | 204.0 |
| Pork Liver Flavor | 5.00 | 100.0 |
| Magnesium Stearate | 1.00 | 20.0 |
| Total | 100.0 | 2000 |

Manufacture Process:
Wet Granulation:
1. Transfer AQUA ZEIN® into a mixing bowl and add dry zein. Use a high shear mixer to mix until powder of dry zein is completely dissolved in AQUA ZEIN®

2. Add glucosamine HCl powder and stir until completely dissolved.
3. Blend Avicel PH102, starch and hydrogenated cottonseed oil in a V-blender and transfer into the mixing bowl and mix.
4. Add Chondroitin Sulfate and mix.
5. Mix to granulate.

Drying:
1. Dry the wet granules into a 60° C. convection oven for about 18 hours.
2. Measure the moisture content (% LOD); make sure granules are dry enough to be milled. Dry for longer time if needed. Target LOD<10%.
3. Pass the partially dried granules through Comil, using a 109G screen.
4. Dry the milled granules further on fluid bed dryer. Dry at 40° C. for 2 hours, then at 60° C. for 2 hours, then at 75° C. for another 60 minutes. Continue to dry at 75° C. in fluid bed drier until % LOD<1%.
5. Mill with a Comil using 079G and 050G screens
6. Pass through a 14 mesh screen.

Blending:
1. Weigh the milled granules.
2. Combine with ESTER-C® and manganese sulfate in a V blender and mix.
3. Add pork liver flavor and mix.
4. Add magnesium Stearate and mix.

Tableting:
1. Compress tablets using the 0.6875 round tooling, target weight 2000 mg, hardness >20 Kp.

Figure 2:
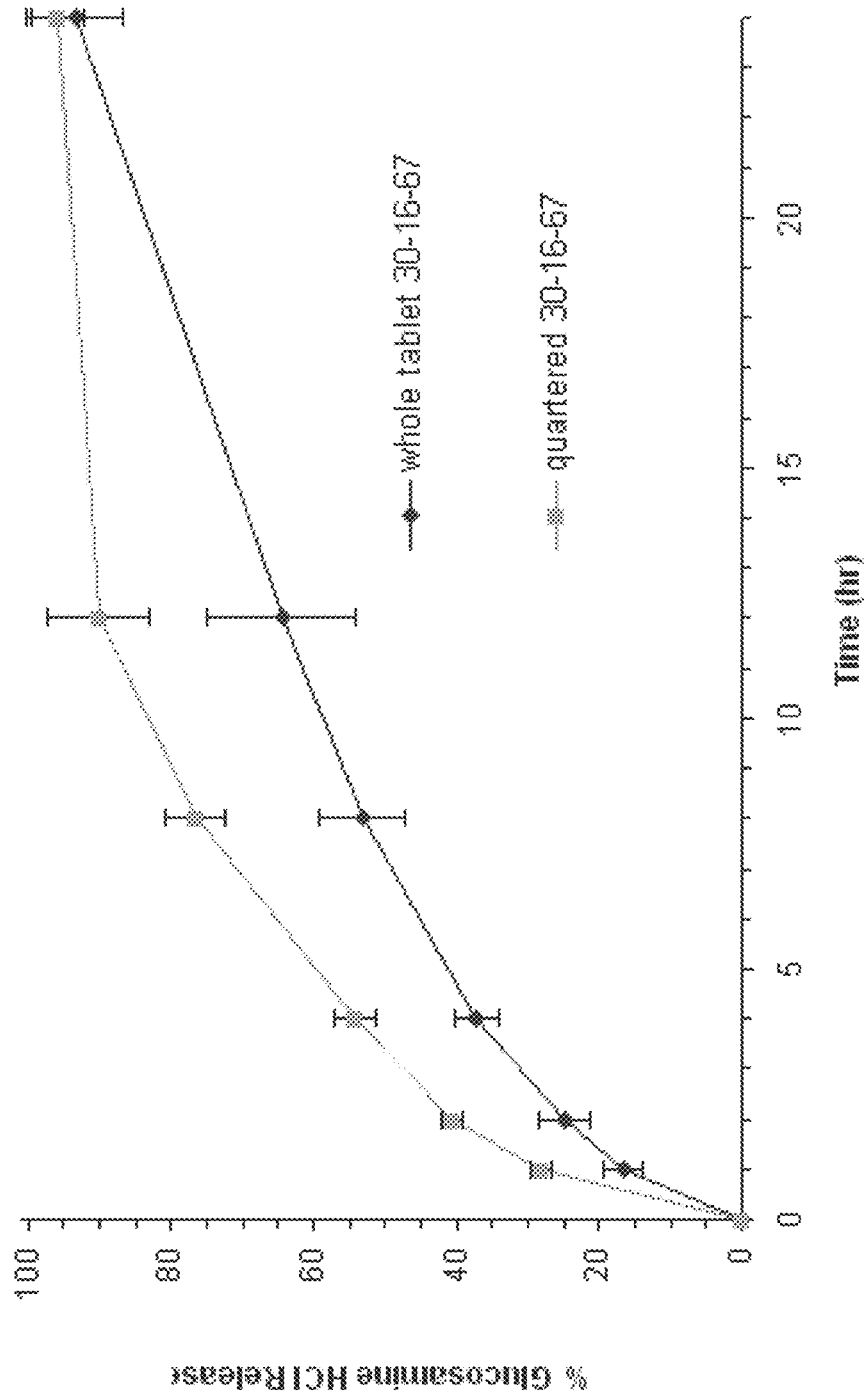
FIG. 2. In vitro release profiles of whole and quartered tablets that contain glucosamine HCl, chondroitin, ESTER-C®, and manganese sulfate prepared according to Example 3.

Results:
The combination of AQUA ZEIN® and hydrogenated cottonseed oil provided sustained release of glucosamine in chewable tablets (24 hours as whole tablets and more than 12 hours as quartered tablets, FIG. 2). Wet granulation process using enriched AQUA ZEIN® was proven feasible to produce granules suitable for manufacturing of these tablets.

Example 4

Chewable and Sustained Release Tablets Containing Vitamins and Minerals

This study was to develop a sustained release (SR) chewable tablet formulation (F-11) for multiple vitamins and minerals. The formulation contained twenty-five vitamin and mineral ingredients selected from three groups including minerals, fat-soluble vitamins and water-soluble vitamins.

The targeted product profile required the tablet to release its active components in a sustained release fashion after being chewed into small fragments. Such SR feature was of particular interest for the water-soluble vitamins as they could be absorbed through a broad section of the gastrointestinal track. The formulation development of the SR chewable tablet thus focused on the release of two water-soluble vitamins (riboflavin and niacinamide). AQUA ZEIN® and carnauba wax were used to form a SR matrix to sequester these two water soluble vitamins and to achieve sustained release dissolution in vitro.

A wet granulation process was developed using a high-shear granulator to incorporate the actives into the SR matrix without using of any organic solvent. This process yielded sustained-release granules, which were subsequently compressed into tablets with certain chewable feature. Such tablets demonstrated sustained release properties in both the chewed and intact forms.

Composition:

The active ingredients in the F-11 formulation consisted of three groups of active mixtures: minerals, fat-soluble vitamins and water-soluble vitamins. These mixtures were sourced from external suppliers as "Premix" in certain fixed compositions. The first and second groups (minerals and fat-soluble vitamins, such as vitamins A, D3, and E) were provided in Premix 1, and the water-soluble vitamins (such as niacin and riboflavin) were in Premix 2. The sustained release granules have the following composition:

TABLE 4A

Sustained Release Granules Composition

| Component | Supplier | % wt, Initial | % wt, Dry (calculated) |
|---|---|---|---|
| AQUA ZEIN ® with Ammonia (an aqueous solution containing 14% zein) | Freeman Industries | 23.65 | 4.16 |
| Zein, USP/NF/FCC | Freeman Industries | 8.40 | 10.54 |
| Premix 2 | Fortitech | 3.55 | 4.45 |
| Carnauba wax, NF | Strahl & Pitsch, Inc | 19.36 | 24.30 |
| Microcrystalline Cellulose, NF (Avicel PH-102) | FMC Biopolymer | 45.04 | 56.55 |
| Total | — | 100 | 100 |

The SR chewable tablet compositions are listed in Tables 4B, 4C and 4D with flavor content at 0%, 2% and 5% w/w, respectively.

TABLE 4B

SR Chewable Tablet Composition (F-11a with no flavor)

| Ingredient | Unit Wt. (mg/tablet) | % (w/w) | Batch Wt. (g) for a 2 kg Batch |
|---|---|---|---|
| SRG | 403.6 | 26.55 | 531.0 |
| Premix 1 | 1100.0 | 72.37 | 1447.4 |
| Magnesium Stearate, NF | 16.4 | 1.08 | 21.6 |
| Total Weight | 1520.0 | 100.0 | 2000 |

TABLE 4C

SR Chewable Tablet Composition (F-11b with 2% flavor)

| Ingredient | Unit Wt. (mg/tablet) | % (w/w) | Batch Wt. (g) for a 2 kg Batch |
|---|---|---|---|
| SRG | 403.6 | 26.02 | 520.4 |
| Premix 1 | 1100.0 | 70.92 | 1418.4 |
| Flavor - vegetarian beef (Fontana Flavors, BVN2390D) | 31.0 | 2.00 | 40.0 |
| Magnesium Stearate, NF | 16.4 | 1.06 | 21.2 |
| Total Weight | 1551.0 | 100.0 | 2000 |

TABLE 4D

SR Chewable Tablet Composition (F-11c/d/e with 5% flavor)

| Ingredient | Unit Wt. (mg/tablet) | % (w/w) | Batch Wt. (g) for a 2 kg Batch |
|---|---|---|---|
| SRG | 403.6 | 25.23 | 504.5 |
| Premix 1 | 1100.0 | 68.75 | 1375.0 |
| Flavor - vegetarian beef/chicken liver (Fontana Flavors, CH5228D)/ pork liver (DSC labs, 808260De1073) | 80.0 | 5.00 | 100.0 |
| Magnesium Stearate, NF | 16.4 | 1.03 | 20.5 |
| Total Weight | 1600.0 | 100.0 | 2000 |

Manufacturing Procedure:

Mixing and High-Shear Granulation:

1. Add AQUA ZEIN® and dry zein powder into a 2 L mixing bowl of the high-shear granulator. Turn on the impeller to mix and to help dissolving zein into AQUA ZEIN®. Mix until a uniform liquid is achieved without any visible solid particles.
2. Add the powder of premix 2 and mix to dissolve it in zein solution.
3. Add carnauba wax and about 70% of Avicel PH102 into the bowl.
4. Start mixing with impeller and chopper.
5. Continue mixing till no visible changes in granule/pellet size, no fine powder
6. Add the remaining Avicel PH102 into the bowl and mix.

Drying:

1. Transfer the product onto drying trays. Place the wet granules/pellets in an oven with air circulation. Dry at about 40° C. for overnight (~18 hours).
2. Sieve the particles by No. 10 screen and collect the particles passed through. For particles retained on the sieve, use the Comil to reduce the size.
3. Combine all milled and sieved granules and continue drying at 40° C. for 1-2 more days.
4. When the moisture content of the granules is below 3%, bring the temperature of the oven up to about 75° C. Dry the granules at 75° C. for 2-3 hours. The moisture content should be at about 1-2% wt.

Sizing and Blending:

1. Pass the dried granules (SRG) through No. 18 screen and collect the portion passed through. Comil the larger particles.
2. Combine all screened SRG granules. Weigh and transfer into a V-blender.
3. Adjust the weights of Premix 1 and flavor according to SRG weight and add both to the V-blender. Mix for 10 minutes.
4. Adjust the weight of magnesium stearate according to the SRG weight and add to the blender. Mix for 2 minutes.

Tableting:

1. Compress the blended powder into tablets with target weight of 1520 mg for F11a, 1551 mg for F11b or 1600 mg for F11c/d/e. Target hardness 6-10 Kp.

Results:

In Vitro Dissolution of SRG

Figure 3:
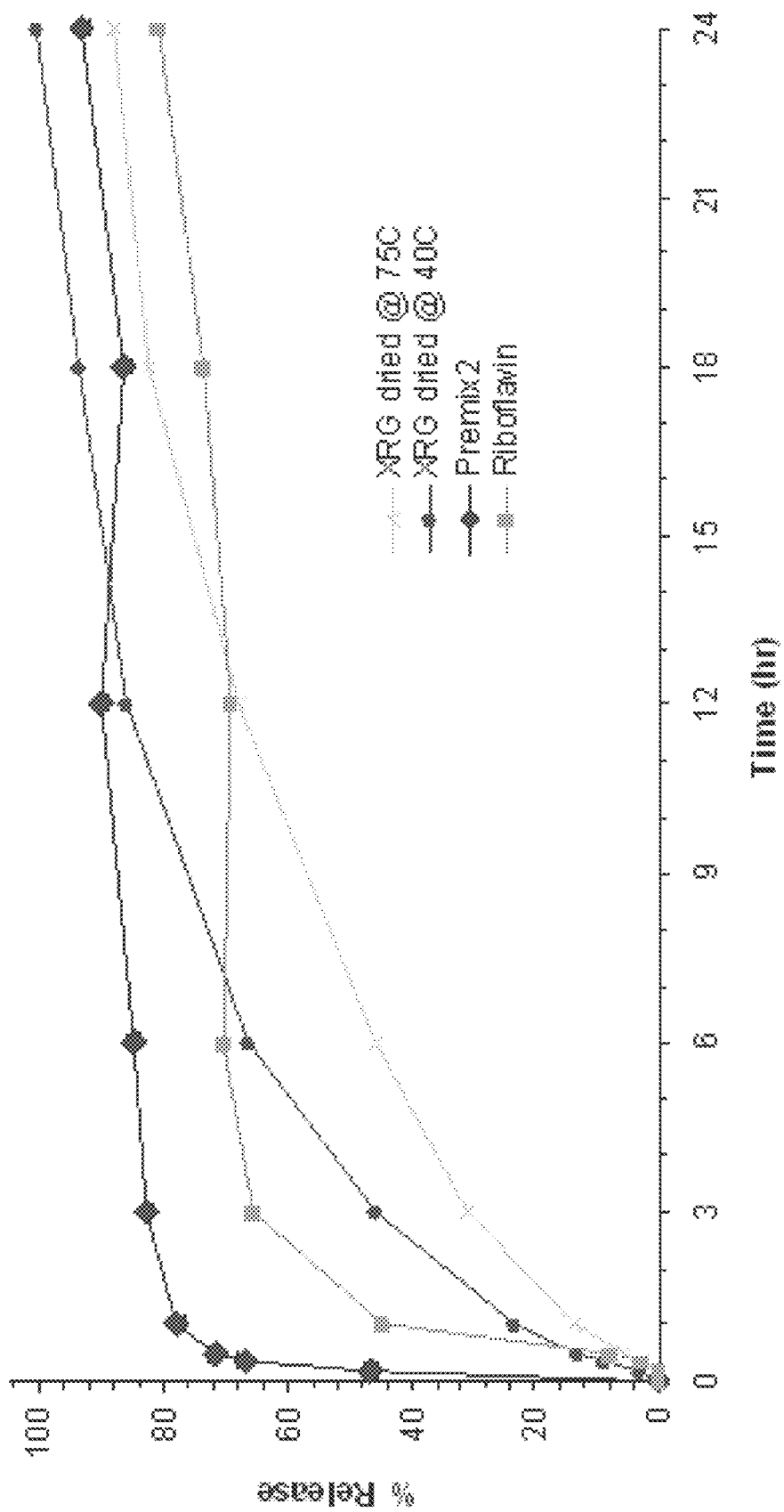
FIG. 3. In vitro dissolution of riboflavin from Sustained Release Granules (SRG) (lot 30-17-29) that contain multi-vitamins and minerals in comparison with raw materials (n=1).

The in vitro dissolution profile of a SRG sample is shown in FIG. 3. Pure riboflavin and Premix 2 were also tested for comparison. The in vitro dissolution profile indicated that the SRG had much slower release than the un-formulated raw materials.

Figure 4:
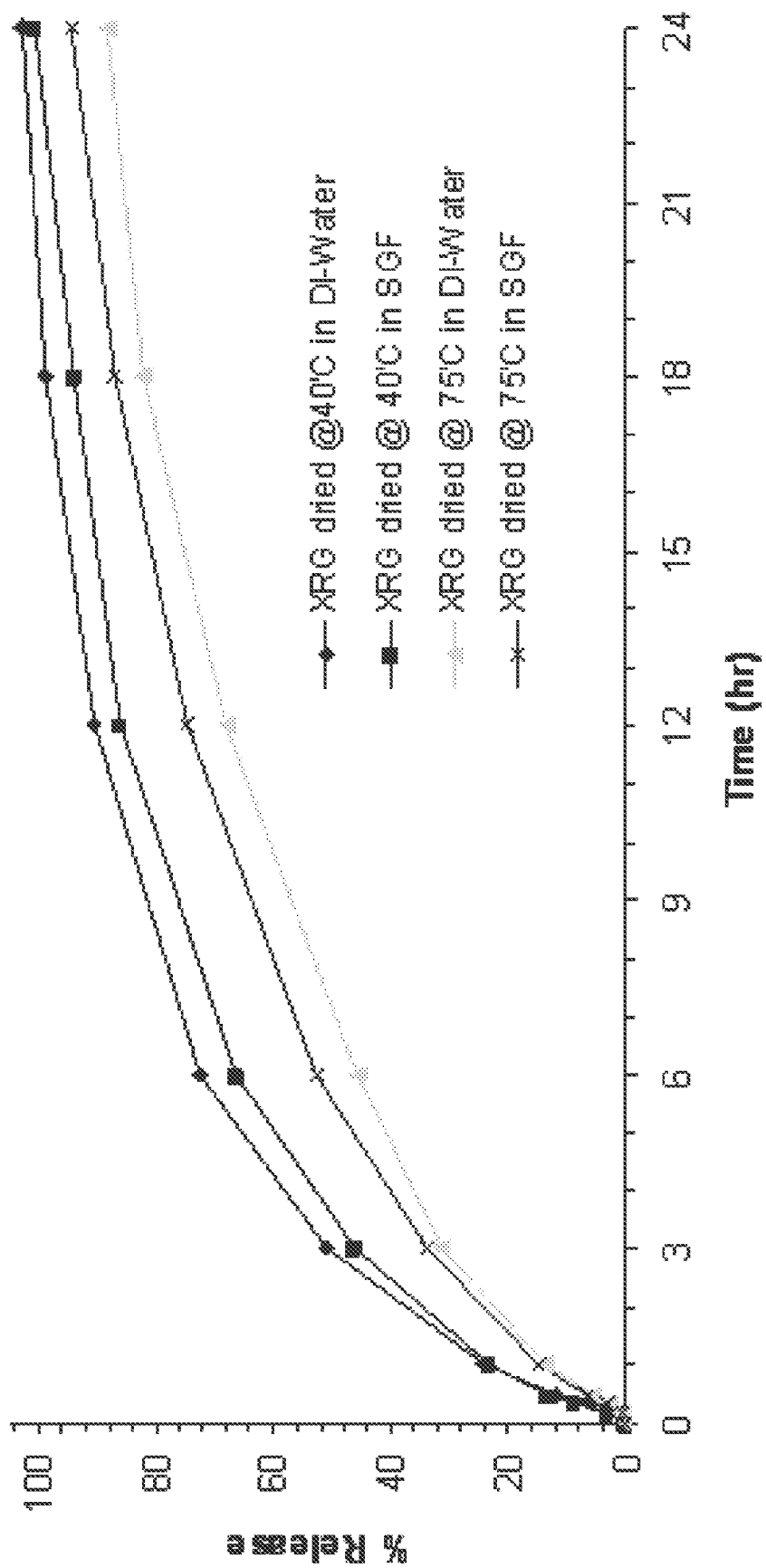
FIG. 4. In vitro dissolution of riboflavin from SRG that contain multi-vitamins and minerals in two different dissolution media (n=1).

The in vitro dissolution profile of SRG with two dissolution media (DI-water and simulated gastric fluid without enzymes (SGF) is shown in FIG. 4.

In Vitro Dissolution of F-11 Tablets

Figure 5:
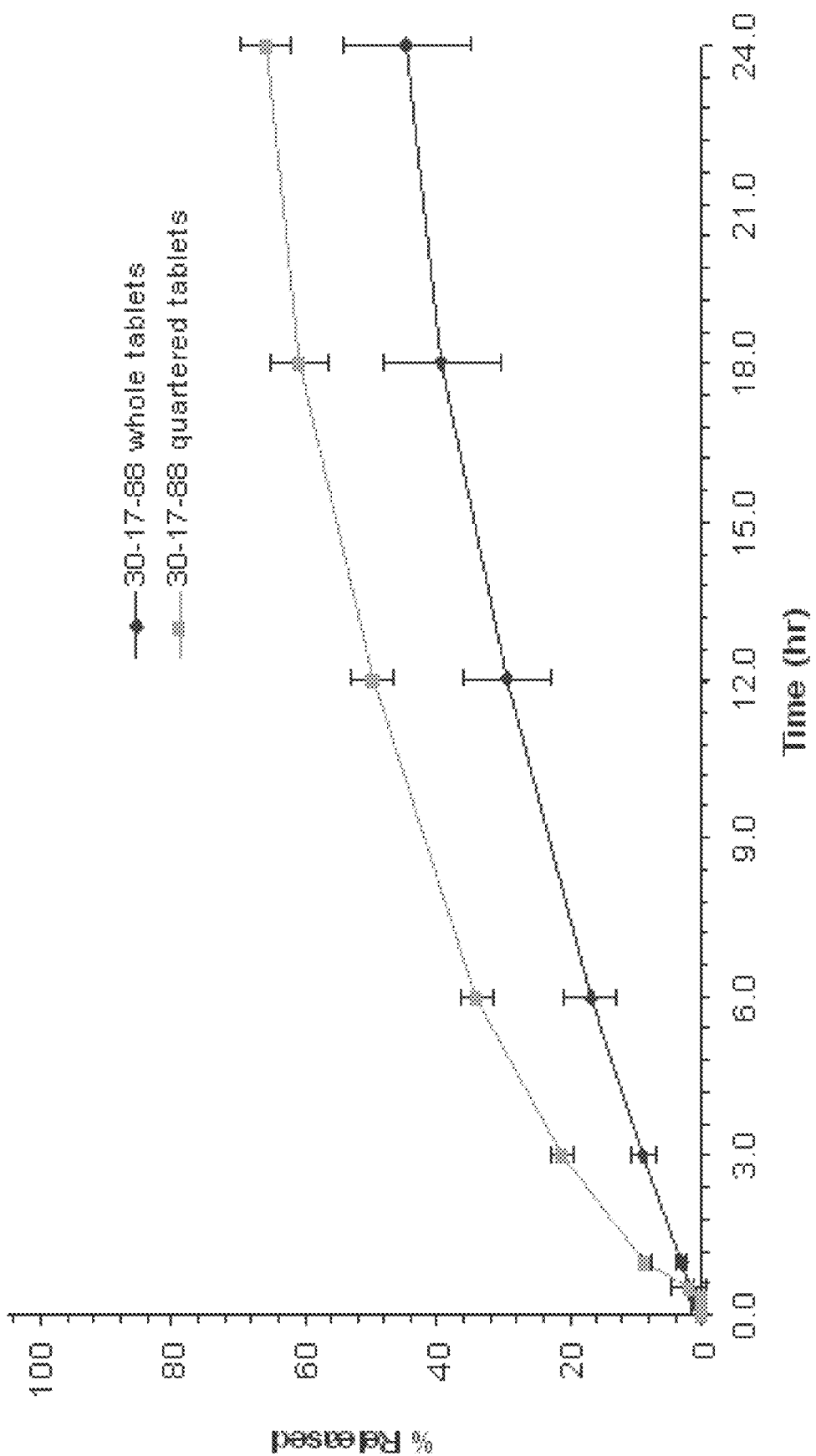
FIG. 5. In vitro release of riboflavin from whole and quartered tablets made from SRG that contain multi-vitamins and minerals (batch 30-17-88) (n=5).

Lot 30-17-88 was prepared and various flavors were added (sub lots 30-17-88a to 30-17-88e). The dissolution profiles for these flavored tablets, both as whole and quartered tablets, are shown in FIG. 5. All tablets displayed release time longer than 24 hours. The slow release profile of the 4-cut (quartered) tablets indicates that the release of riboflavin is mainly controlled by the SRG, which remains intact even after the tablets are broken down. Therefore these tablets can be expected to provide slow release of the water-soluble vitamins after being chewed into small fragments.

Figure 6:
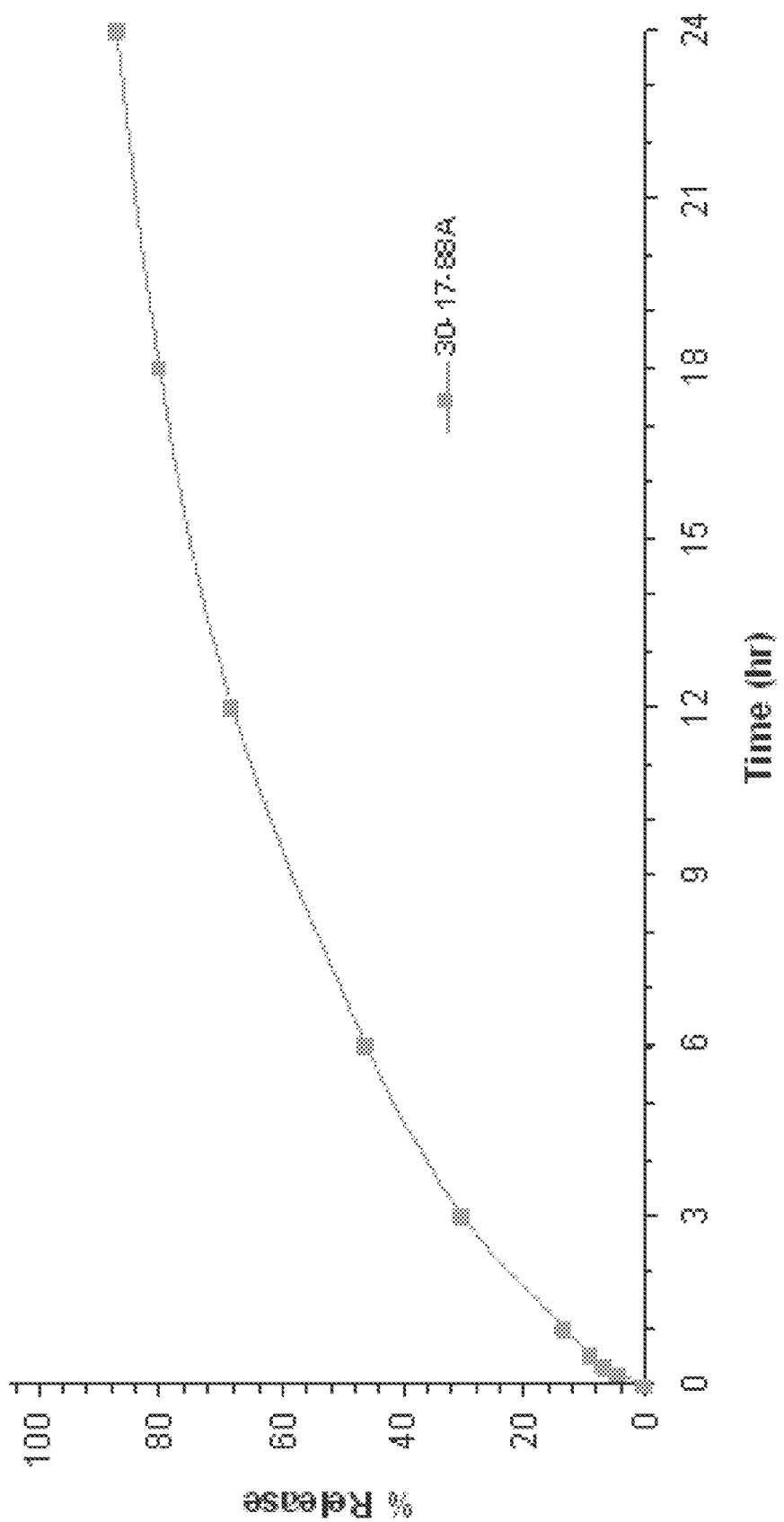
FIG. 6. In vitro release of niacinamide from whole tablets made from SRG that contain multi-vitamins and minerals (batch 30-17-88A) (n=1).

Release of niacinamide was also monitored. The in vitro release profile of niacinamide for batch 30-17-88a is shown in FIG. 6.

The above results showed that the F-11 formulation using zein and carnauba wax as release control agents achieved targeted in vitro dissolution profile with both riboflavin and niacinamide achieved 24 hour in vitro dissolution with minimal burst, as whole tablets or quartered tablets.

Example 5

Sustained Release Chewable Tablets that Containing Glucosamine HCl

This study was to develop chewable sustained release tablets for glucosamine.

Study A—Developing 1.2 mm Glucosamine SR Noodle Formulation for Chewable Tablets Compositions:

TABLE 5A 1.2 mm SR noodles

| Component | g/batch | % w/w |
|---|---|---|
| In wet mass | | |
| Glucosamine HCl | 325 | 44.5 |
| Microcrystalline Cellulose (AVICEL PH102) | 45 | 6.2 |
| Pregelatinized Starch (Starch 1500) | 30 | 4.1 |
| Hydrogenated Cottonseed Oil (sterotex) | 100 | 13.7 |
| AQUA ZEIN ® (14% solid) | 75 | 10.3 |
| Deionized water | 155 | 21.2 |
| Total | 730 | 100.0 |
| In dry mass | | |
| Glucosamine HCl | 325 | 63.7 |
| Avicel PH102 | 45 | 8.8 |
| Starch 1500 | 30 | 5.9 |
| Hydrogenated Cottonseed Oil | 100 | 19.6 |
| Zein | 10.5 | 2.0 |
| Total | 510.5 | 100.0 |

Manufacturing Process:

A process similar to Example 1 was followed.

Results

Figure 7:
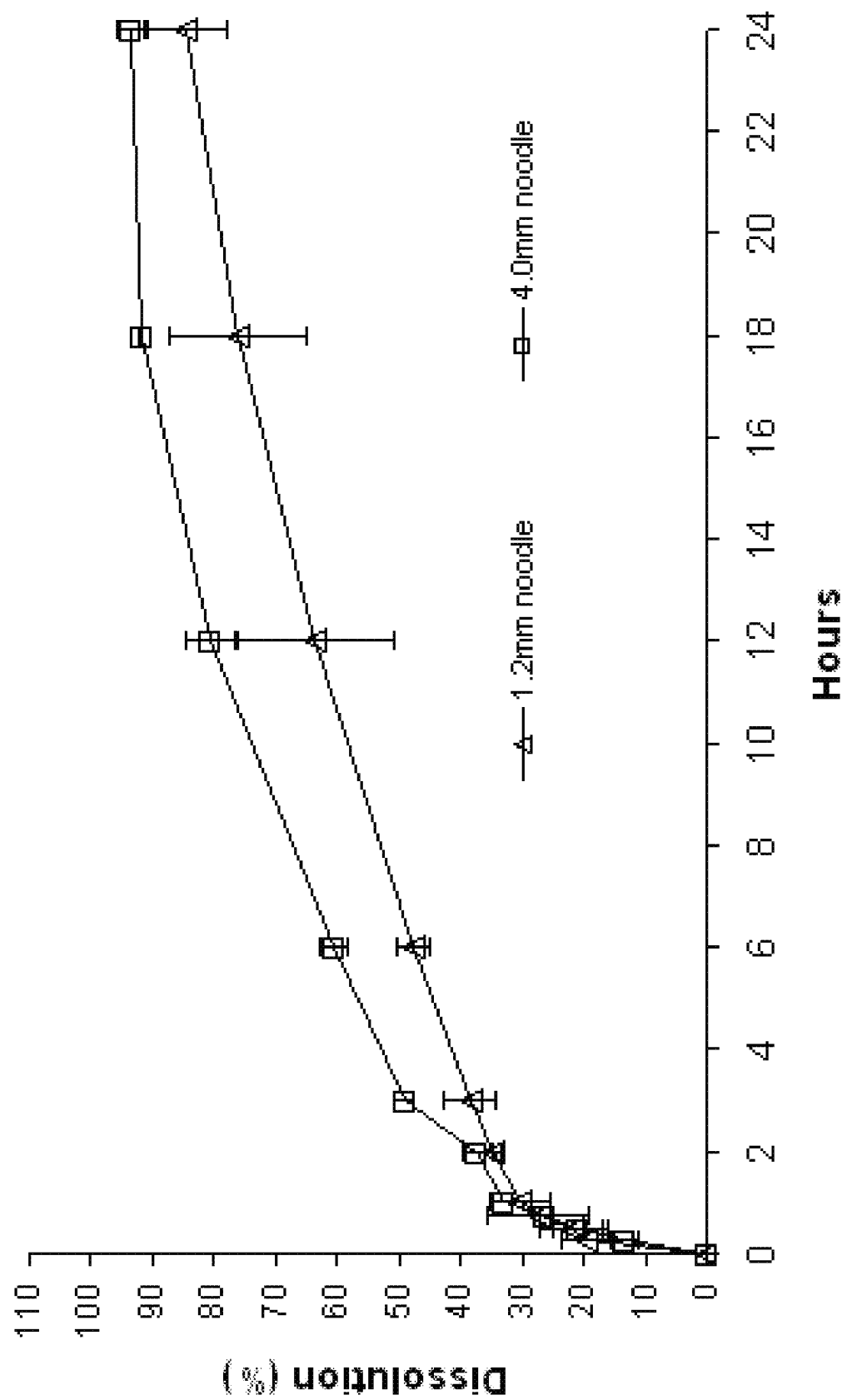
FIG. 7. In vitro dissolution of glucosamine HCl from 1.2 mm and 4.0 mm AQUA ZEIN® noodles.

The in vitro dissolution of glucosamine HCl from the 1.2 mm AQUA ZEIN® noodles, a 4 mm AQUA ZEIN® noodles prepared according to Example 7 are shown in FIG. 7. The 1.2 mm AQUA ZEIN® noodles exhibited an extended dissolution profile with about 35% release in the first 2 hours. The 1.2 mm noodles are relatively hard and seem to be well suited for incorporating into chewable tablets. The 4 mm AQUA ZEIN® noodles also exhibited an acceptable dissolution profile.

Study B—Preparing Chewable Tablets from 1.2 mm Glucosamine SR Noodle Formulation Composition

TABLE 5B

Tablet composition table based on the 1.2 mm AQUA ZEIN ® noodles

| Composition | F-12 | | |
|---|---|---|---|
| | % w/w | Per tablet (mg)* | Per batch of 375 tab (g) |
| 1.2 mm noodles containing about 56.6% w/w glucosamine HCl with 14% AQUA ZEIN ® | 44.2 | 883.4* | 331.5 |
| 1.2 mm blank noodlets with 14% AQUA ZEIN ® | 53.8 | 1076.6 | 403.5 |
| Pork liver powder | 1 | 20 | 7.5 |
| Magnesium stearate | 1 | 20 | 7.5 |
| Total | 100 | 2000 | 750 |

*Glucosamine HCl strength = 25% w/w or 500 mg per tab

Preparation
1. Pass the glucosamine noodles & blank noodle thru a 10 mesh sieve.
2. Weigh out glucosamine noodles & blank noodles into a V-blender, mix for 30 min.
3. Add liver favor & magnesium stearate and mix for 2 min.
4. Compress to tablets using the "2000 mg round tooling" to max hardness.
5. Observe the powder flowability.
6. Record tablet weight, hardness and friability.
7. Test for dissolution.

Figure 8:
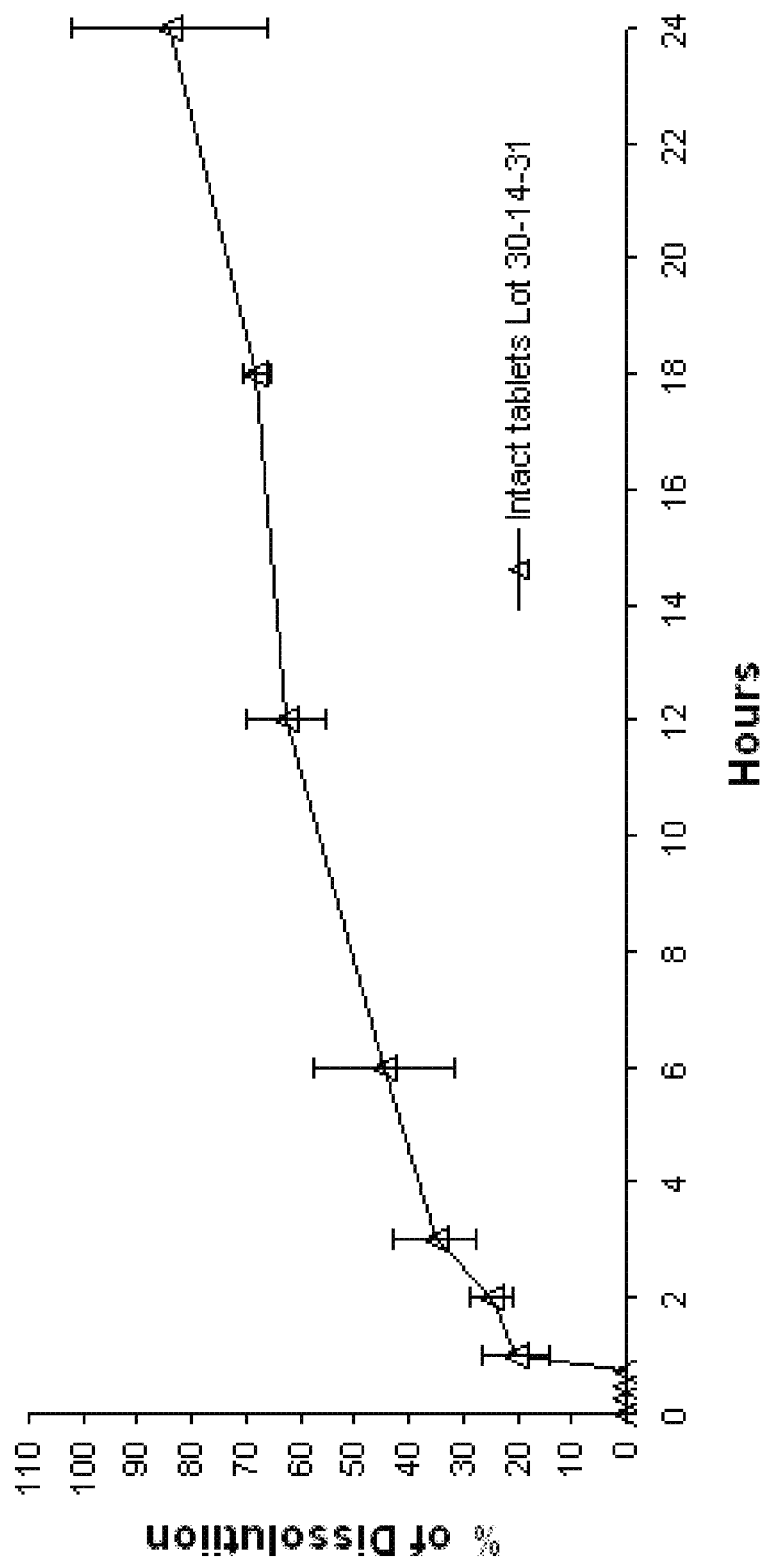
FIG. 8. In vitro dissolution of glucosamine HCl from chewable tablets prepared from 1.2 mm AQUA ZEIN® noodles.

Results:

In vitro dissolution of glucosamine sustained release chewable tablets made with F12 showed sustained release with less than 50% release in the first 2 hours (FIG. 8).

Example 6

Taste-Masked and Sustained Release Tramadol Hydrochloride Pellet Formulation

This study was to develop a taste-masked and sustained release pellet formulation containing tramadol HCl. The mini-pellets were small cylindrical rods with a diameter of about 0.87 mm and average length of about 2.5 to 3 mm ("mini-pellet"). The mini-pellet dosage form was selected because they could be easily measured out for a given dose by weight or volume and mixed with animal (e.g., a cat) feed to allow for voluntary consumption by animals for analgesic effects. Due to the extremely high sensitivity and selectivity of certain animals (e.g., cats) to their feed, one of the primary objectives in developing the mini-pellet formulation was to mask the bitter taste of tramadol such that animals would take the mini-pellets voluntarily after being mixed with animal food. In addition, the sustained release property was also desired for the mini-pellets to provide once-a-day dosing for dosing convenience and better compliance.

Two main approaches were used to mask the bitter taste of the highly water soluble tramadol HCl. The first step was to form non-disintegrating core pellets, and the second step involved coating a layer of wax-like material on the core pellets to further reduce drug release and at the same time adding a flavor in the coating.

Two final formulations (F-26 and F-29) were tested in cats and were found to be acceptable to cats, i.e. all test cats consumed them voluntarily. F-29 was selected as the prototype formulation for further development based on it superior in vitro release property.

Composition

Tables 6A to 6D provide compositions of F-26 and F-29. A common core pellets were prepared and then coated with additional hydrogenated cottonseed oil containing a pork liver flavor for F-26 or tuna flavor for F-29.

TABLE 6A

Core Pellet Composition (shared by F-26 and F-29)

| Ingredient | % (w/w) |
|---|---|
| Tramadol HCl | 20.00 |
| Microcrystalline Cellulose | 55.50 |
| Pregelatinized Starch | 5.00 |
| Hydrogenated Cottonseed Oil (HCSO) | 9.50 |
| Zein (from AQUA ZEIN ®) | 10.00 |
| Total | 100.0 |

TABLE 6B

Final Coated Pellets Compositions, % w/w

| Ingredient | F-26 | F-29 |
|---|---|---|
| Tramadol HCl | 10.00 | 10.00 |
| Microcrystalline Cellulose | 27.75 | 27.75 |
| Pregelatinized Starch | 2.50 | 2.50 |
| HCSO in core | 4.75 | 4.75 |
| Zein | 5.00 | 5.00 |
| HCSO in coating | 45.20 | 45.20 |
| Pork Liver Flavor | 4.80 | — |
| Tuna Flavor | — | 4.80 |
| Total | 100.0 | 100.0 |

Manufacture Process:
Core Pellets
1. Transfer AQUA ZEIN® into the mixing bowl, gradually add Tramadol HCl, dissolve it completely by mixing.
2. Blend Avicel PH102, starch 1500 and hydrogenated cottonseed oil (HCSO) using a V-blender for 5 minutes.
3. Gradually add the blend to the mixing bowl, mix until uniform dough is obtained with target moisture content of about 35%.
4. Extrude the dough through a 0.8 mm screen twice.
5. Place the wet noodle (extrudates) in a 60° C. oven overnight to remove moisture to about 5.5%.
6. Break the dry noodles into core pellets by a Co-mil running with a 050G sieve.
7. Further dry the pellets in a Fluid Bed Dryer for 10 minutes at 40° C. then 40 minutes at 75° C. to moisture level less than 1%.
8. Sieve the pellets by a #45 mesh screen to remove fine powder. Collect intact pellets (the Core Pellets).

Coated Pellets
1. Melt HCSO in an oil bath at about 75° C.
2. Heat the stainless steel mixing bowl with hot air to about 55° C. (+/−3).

3. Add the core pellets into the bowl and stir. The pellet bed temperature is about 50° C.
4. Once pellet bed temperature is steady, add the molten HCSO in a thin stream onto the pellet bed using syringe pump while stirring.
5. Stop wax addition and stir 10 minutes occasionally. Increase the mixing speed as needed to prevent clumping and allow for even distribution of the coating.
6. After the total amount of HCSO is added, add the flavor and continue to mix for 5 min.
7. Turn off heat source and continue mixing the pellets until they are no longer "wet" on touching.
8. Sieve the coated pellets through a #10 mesh screen. Remove the large chunks.
9. Sieve the coated pellets through a #35 mesh screen. Remove the fine powder.

In Vitro Release Methods

Two in-vitro release methods were developed and used. Method A was used for quick comparison of tramadol initial burst release from the pellets.

TABLE 6C

Dissolution Method A

| | |
|---|---|
| Apparatus | 50 mL Falcon Tube |
| Medium | DI-water |
| Volume | 40 mL |
| Temperature | RT |
| Stirring speed | 25 gentle inversions by hand in one minute, then inversion by hand one minute before each time point |
| Sample volume | 1 mL (without replenishment of fresh medium). Each sample was filtered through a 1.2-micron filter prior to filling into an HPLC vial. |
| Conc assay | HPLC |

A standard dissolution method was developed and used for the final formulations F-26 and F-29 (Method B). This method was intended for comparing both initial burst release and sustained release profile using the standard USP dissolution apparatus.

TABLE 6D

Dissolution Method B

| | |
|---|---|
| Apparatus | USP I (basket) |
| Medium | Simulated Gastric Fluid (SGF), without enzyme |
| Volume | 1000 mL |
| Temperature | 37° C. |
| Stirring speed | 50 rpm |
| Sample volume | 1 mL (without replenishment of fresh medium). Each sample was filtered through a 30-micron filter prior to filling into an HPLC vial. |
| Conc assay | HPLC |

Results

Figure 9:
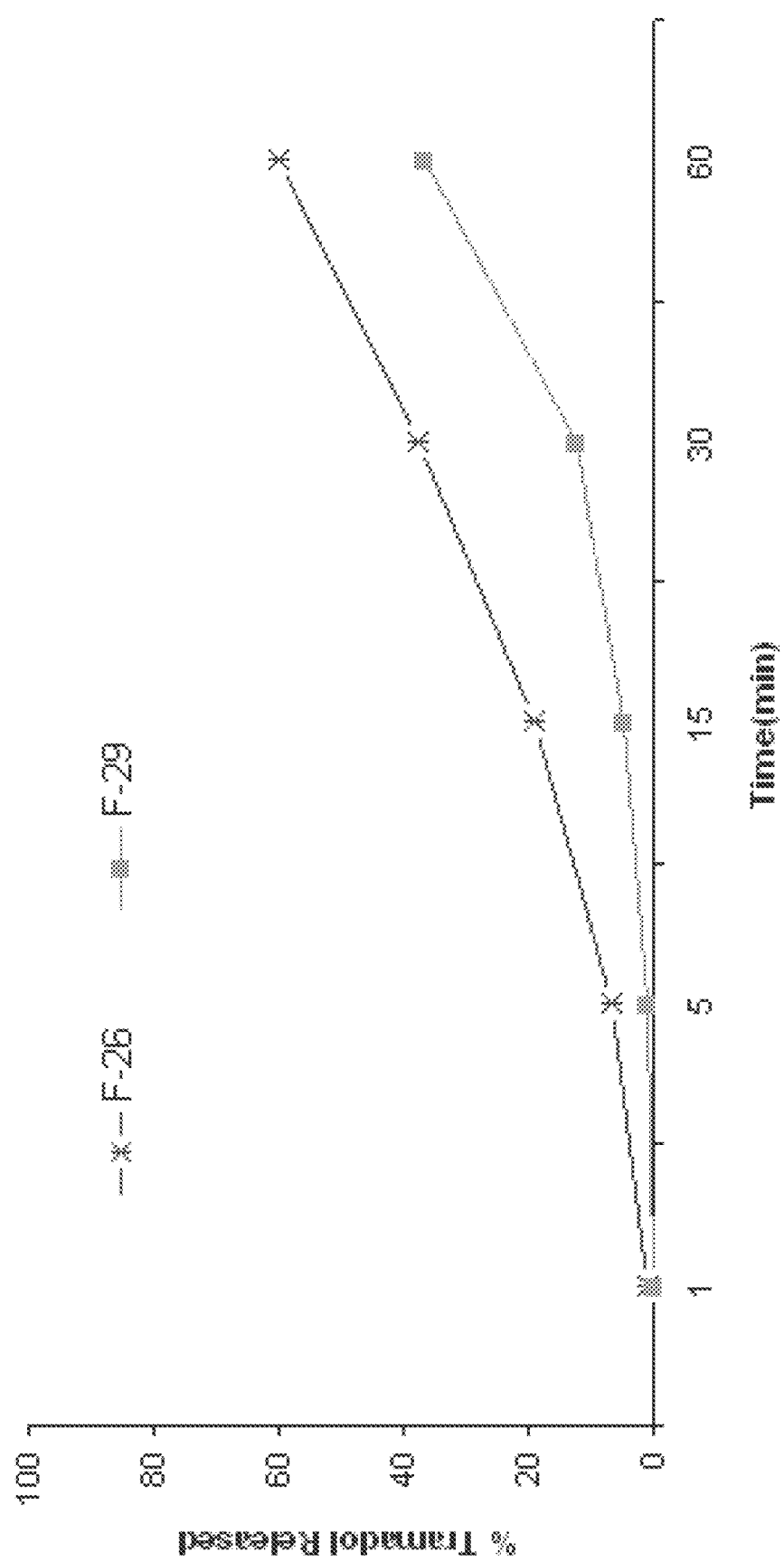
FIG. 9. In vitro initial tramadol release profiles of coated tramadol-containing pellets F-26 and F-29 by dissolution Method A as described in Example 6.

The in vitro release profiles of F-26 and F-29 by Method A are shown in FIG. 9. Both F-26 and F-29 exhibited subdued initial burst release in the first 5 minutes, which is believed to be critical for taste masking.

Figure 10:
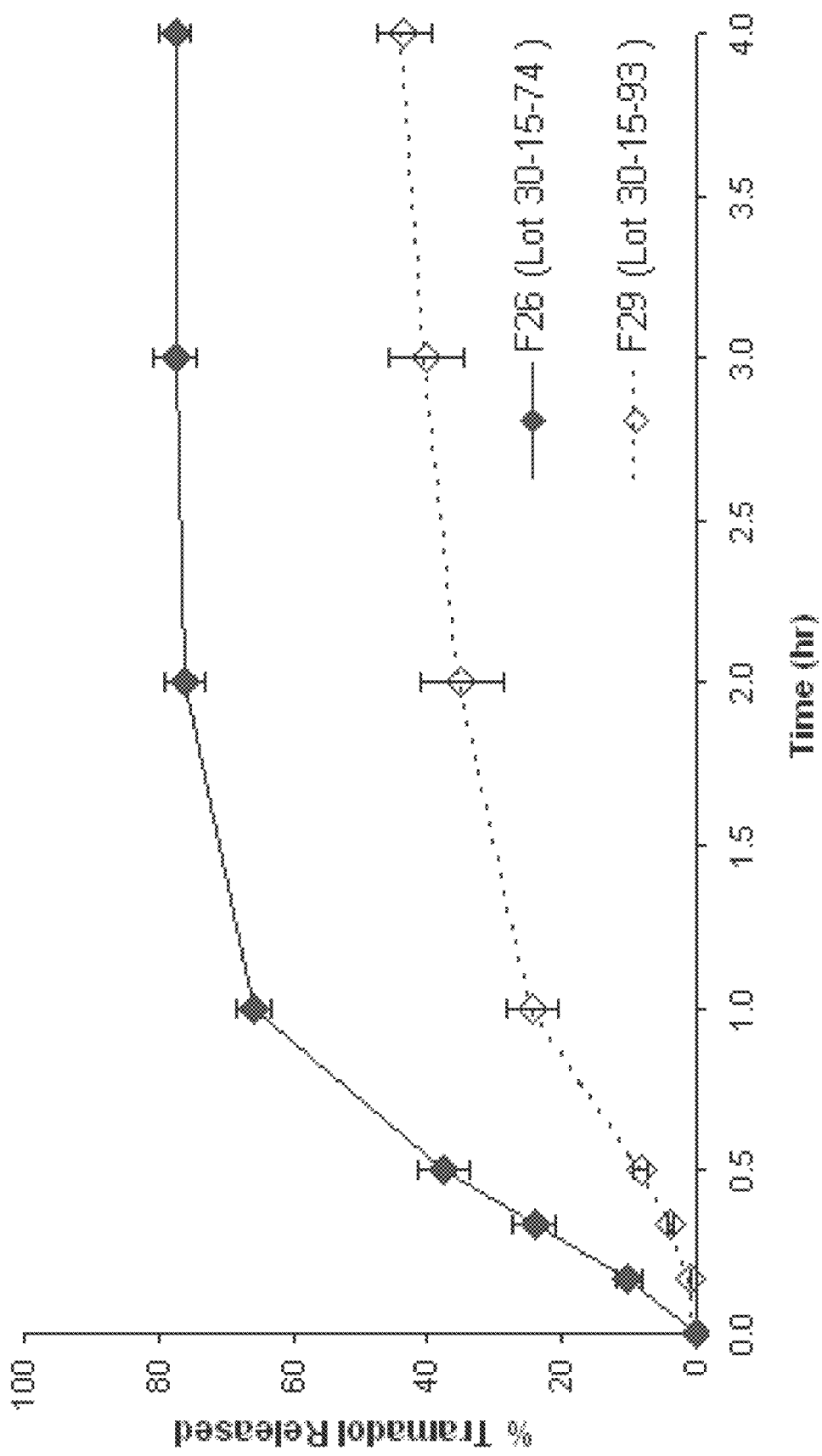
FIG. 10. In vitro tramadol release profiles of coated tramadol-containing pellets F-26 and F-29 by dissolution Method B as described in Example 6.

The results obtained by Method B showed similar relative release rate in the first hour as compared to the results from method A, where no strong burst was detected for F-29 in the first 5 minutes (FIG. 10). In addition, F-29 exhibited a sustained release feature under the standard USP dissolution testing method.

The above results indicate that F-29 mini-pellet formulation seemed to be well accepted (eaten voluntarily) by cats after being mixed with a commercial brand semi-moist food. This suggests that the non-disintegrating core and HCSO coating fulfilled their purpose of masking the taste of tramadol. The slow in vitro release profile by the standard USP dissolution method indicates that sustained in vivo release or prolonged duration of analgesic action may be expected.

Example 7

4 Mm Diameter Glucosamine HCl Sustained Release Pellets

This study was to develop a formulation and a process to make glucosamine 4 mm diameter sustained release pellets ("noodles" or "noodlets") for administering to animals, especially to horses.

Compositions:

TABLE 7A

Final composition (in wet dough)

| Component | % w/w | mg/unit |
|---|---|---|
| Glucosamine HCl | 40.93 | 650 |
| Microcrystalline Cellulose | 5.67 | 90 |
| Pregelatinized Starch | 3.78 | 60 |
| Hydrogenated Cottonseed Oil | 12.59 | 200 |
| AQUA ZEIN ® (14% solid w/w) | 9.45 | 150 |
| Deionized water | 27.58 | 438 |
| Total | 100 | 1588 |

TABLE 7B

Final composition (in dry pellets)

| Component | % w/w | mg/unit |
|---|---|---|
| Glucosamine HCl | 63.66 | 650 |
| Microcrystalline Cellulose | 8.81 | 90 |
| Pregelatinized Starch | 5.88 | 60 |
| Hydrogenated Cottonseed Oil | 19.59 | 200 |
| Zein | 2.06 | 21 |
| Total | 100 | 1021 |

Manufacture Process:
1. Transfer Glucosamine HCl into the mixing bowl, turn on the mixer for 5 minutes to obtain a uniform powder blend. While mixing, gradually add AQUA ZEIN®.
2. Transfer Avicel PH102 and Starch 1500 into the mixing bowl and mix for 2 minutes.
3. Transfer Sterotex into the mixing bowl and mix for 2 minutes.
4. Add deionized water into the mixing bowl and mix for about 5-10 minutes to obtain uniform wet dough. Water content in the dough should be between 26% and 30% w/w as determined by a moisture balance.
5. Feed the dough continually into the extruder and extrude thru a 4 mm dome sieve.
6. Collect extrudates ("noodles") in a plastic tray.
7. Place the pellets in an ambient open-air area for 16-24 hours.
8. Transfer the pellets into an oven and set temperature at 40° C. for 10-12 hours.
9. Raise the temperature to 60° C. for 2 hours.
10. Transfer the pellets into a fluid bed dryer.
11. Set dryer temperature at 75° C. and set sufficient airflow to fluidize the pellets. Dry the pellets for 60-90 minutes.

12. Measure the moisture of the pellets by moisture analyzer.
13. Stop drying when the moisture is 1% w/w.
14. Collect the dried pellets into a moisture-proof container.

Figure 11:
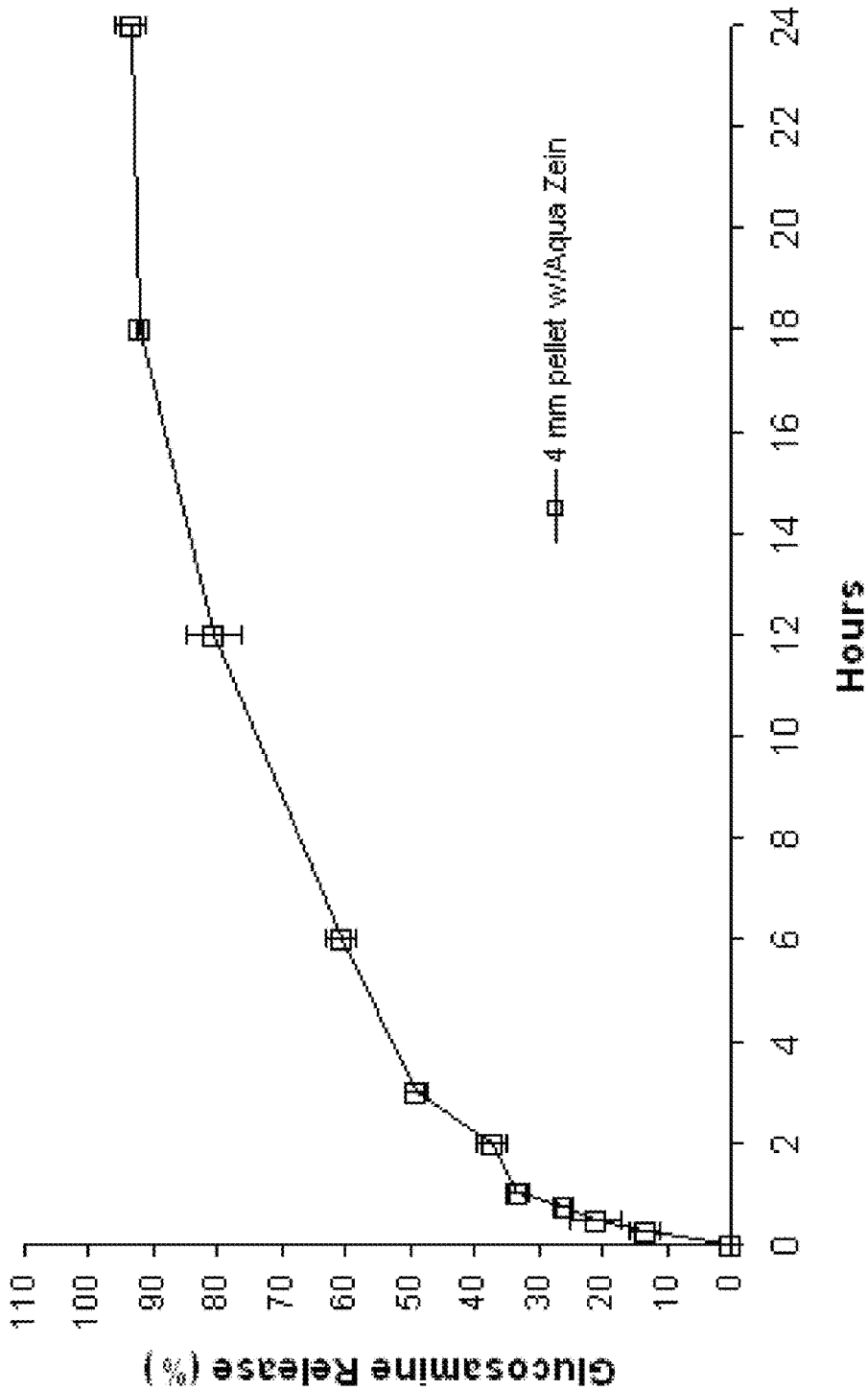
FIG. 11. In vitro dissolution of 4 mm glucosamine-containing AQUA ZEIN® pellets.
Figure 12:
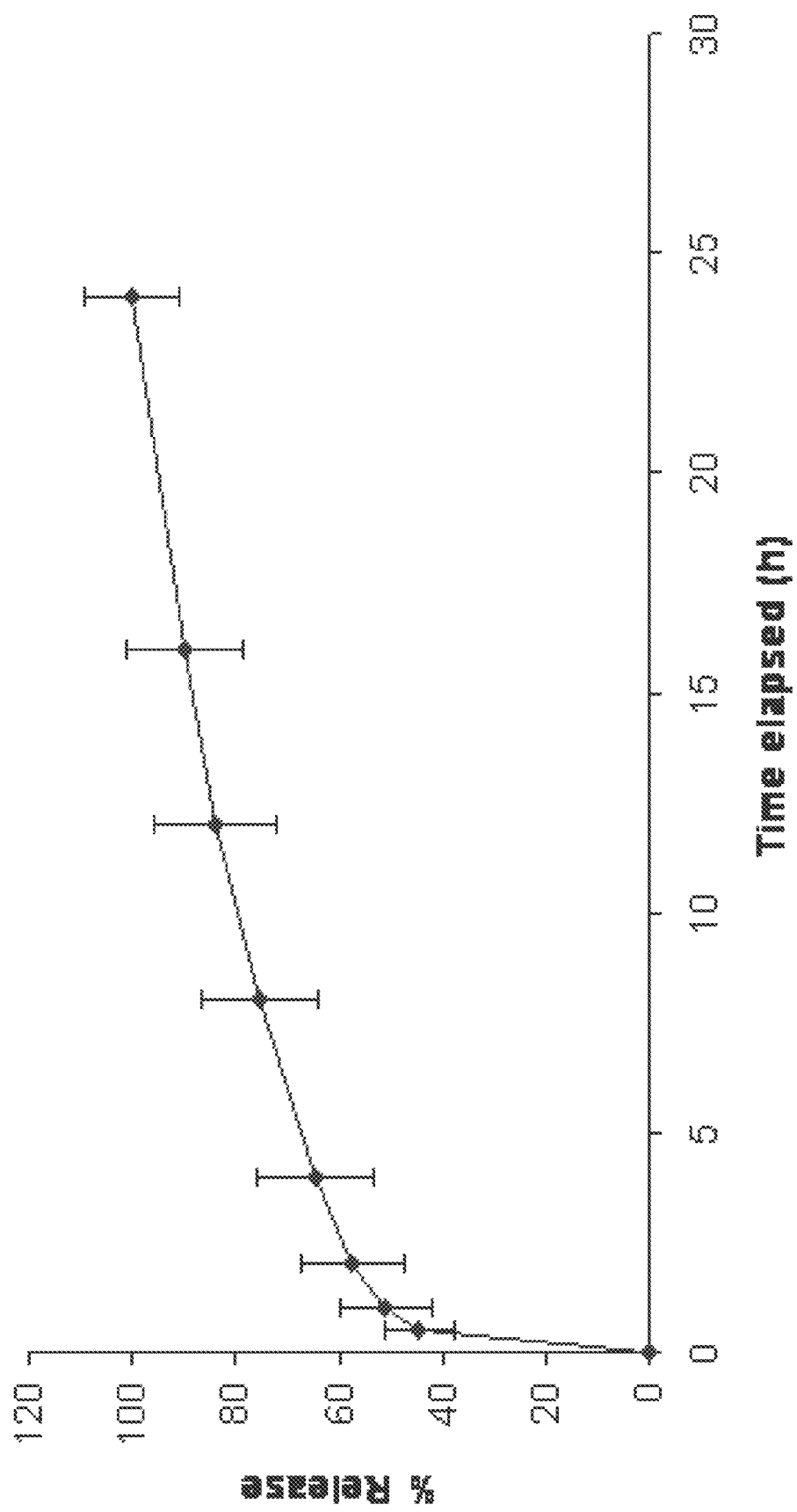
FIG. 12. In vitro dissolution of tramadol from tramadol-containing beadlets prepared according to Example 8.

Results:

In vitro dissolution study shows that the 4 mm diameter glucosamine HCl SR pellets formulation released no more than 50% of tramadol in the first 2 hours and no less than 80% within 24 hours (FIG. 11).

Example 8

Preparing Tramadol Beadlets with High Shear Granulation Process

This study was to prepare beadlets by high-shear granulation process.

Composition:

TABLE 8A

| Granules | | |
|---|---|---|
| Component | % w/w in wet mass | % w/w in dry mass |
| Tramadol HCl | 18.0 | 20.5 |
| Microcrystalline Cellulose PH200 | 20.3 | 23.1 |
| Carnauba wax | 27.0 | 30.9 |
| Dry Zein | 20.3 | 25.5 |
| AQUA ZEIN ® (14% solid w/w) | 14.5 | |
| Total | 100 | 100 |

TABLE 8B

| Coated granule | |
|---|---|
| Component | % w/w |
| Granules from Table 8A | 60 |
| Hydrogenated cottonseed oil (HCSO) | 40 |

Manufacture Process:

Granulation Step
1. Add Tramadol and AQUA ZEIN® in the mixing bowl of granulator, and mix to dissolve Tramadol in AQUA ZEIN®.
2. Add Avicel PH102, Carnauba wax, and dry Zein into the mixing bowl.
3. Mix by impeller and chopper, stop occasionally to scrap powder from bottom and side of bowl.
4. Continue mixing till no visible changes in granule/pellet size, no fine powder.

Drying
1. Transfer the granules onto drying trays. Place the wet granules/pellets in an oven with air circulation. Dry at about 40° C. for overnight (~18 hours).
2. Sieve the particles by #10 screen and collect the particles passed through. For particles retained on the sieve, use the Comil to reduce the size.
3. Combine all milled and sieved granules and continue drying at 40° C. for 1-2 more days.
4. When the moisture content of the granules is below 3%, bring the temperature of the oven up to about 75° C. Dry the granules at 75° C. for 2-3 hours.

Sizing
1. Pass the dried granules through #18 screen and collect the portion passed through. Comil the larger particles.
2. Combine all screened granules.

Coating
1. Transfer the granules into a coating pan and start rotating.
2. Add molten HCSO slowly to the particles, spread evenly, avoid over-wetting.
3. Stop addition of HCSO occasionally to allow granules to cool down and surface HCSO to solidify.
4. After all HCSO are added, continue rotating for 10-20 minutes to allow HCSO to solidify.
5. Pass coated particles through #14 (1.4 mm) screen to de-lump and #30 screen (0.59 mm) to remove fines.

Results

Figure 13:
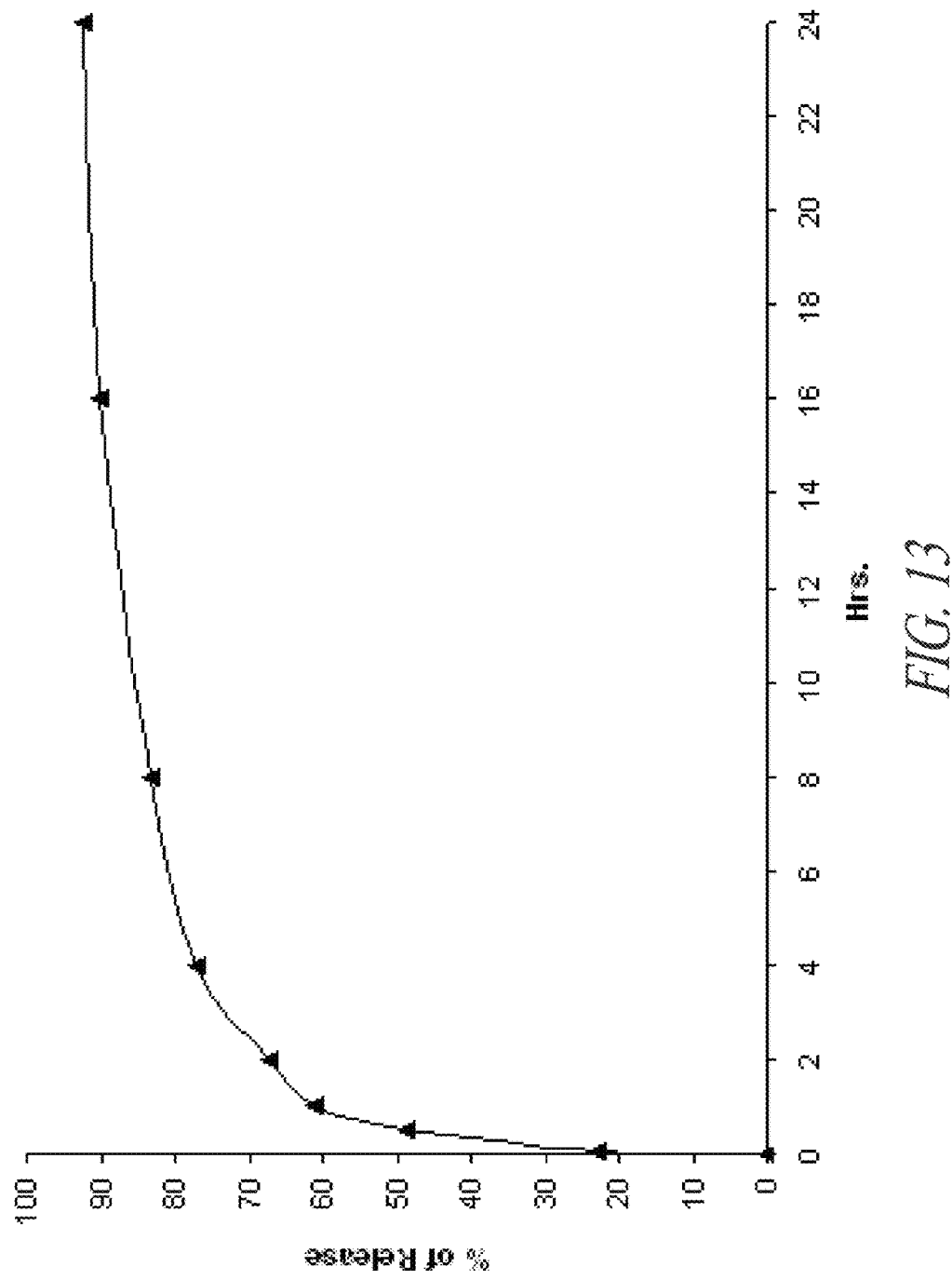
FIG. 13. In vitro dissolution of tramadol from tramadol-containing granules prepared according to Example 9.
Figure 14:
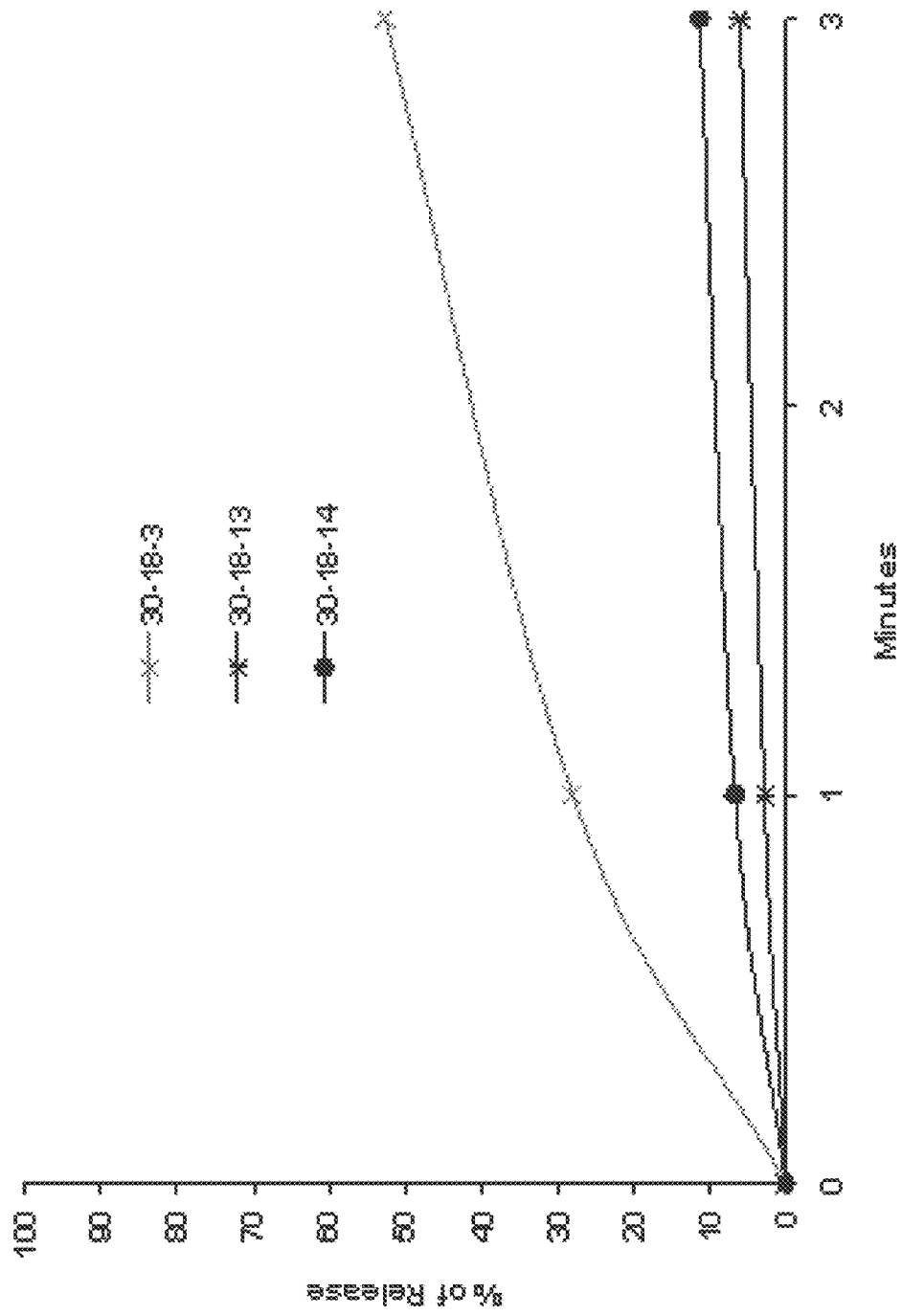
FIG. 14. In vitro initial dissolution of tramadol-containing granules prepared according to Example 9.

The In vitro dissolution study showed that the uncoated granules exhibited a sustained release for 12-24 hours (FIG. 13), but initial burst (3 minutes) was high (FIG. 14, lot 30-18-3). The coated granules showed a much reduced initial burst (FIG. 14, lots 30-18-13 and 30-18-14, two particle sizes).

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A chewable, sustained release pharmaceutical composition in the form of multiparticulates, each multiparticulate having an insoluble solid core, wherein said composition consisting of:
   (a) from about 0.5% to about 20% by weight of an active ingredient, wherein the active agent is phenylpropanolamine hydrochloride;
   (b) from about 0.5% to about 10% by weight of zein from an aqueous dispersion of zein, wherein the active ingredient and zein form the insoluble solid core of the multiparticulates;
   (c) from about 20% to about 80% by weight of a wax-like agent, wherein the wax-Eke agent is hydrogenated vegetable oil, which seals cracks and crevasses within the insoluble solid core of the multiparticulates, wherein the insoluble solid core is sealed by the wax-like agent at temperatures ranging from about 60° C. to about 75° C.;
   (d) from about 10% to about 40% by weight of microcrystalline cellulose and from about 5% to about 25% by weight of pregelatinized starch, which is mixed with the insoluble solid core of the multiparticulates;
   (e) from about 2% to about 5% by weight of flavor; and
   (f) from about 1% to about 2% by weight of lubricant, wherein particle size of each multiparticulate is from about 0.1 mm to about 4 mm, and wherein (i) the multiparticulates having insoluble solid cores have a water content of no more than 3% relative to the total weight of the multiparticulates; (ii) the composition is in the form of multiparticulates or multiparticulates embedded into tablets; (iii) the tablets or multiparticulates are optionally coated with a sustained release barrier coating; and (iv) the composition has an in vitro dissolution rate of the active ingredient measured by standard USP basket method of at most 90% of the active ingredient released after 2 hours, wherein the in vitro dissolution rate of the active ingredient does not require the sustained release barrier coating on the multiparticulates or tablets.

2. The composition of claim 1, consisting of:
(a) about 1.24% by weight of phenylpropanolamine hydrochloride;
(b) about 2.35% by weight of zein from an aqueous dispersion of zein;
(c) about 49.35% by weight of the wax-like agent;
(d) about 26.96% by weight of microcrystalline cellulose and about 14.10% by weight pregelatinized starch;
(e) about 5% by weight of flavor; and
(f) about 1% by weight of lubricant.

3. The composition of claim 1, consisting of:
(a) about 4.70% by weight of phenylpropanolamine hydrochloride;
(b) about 2.35% by weight of zein from an aqueous dispersion of zein;
(c) about 49.35% by weight of hydrogenated vegetable oil;
(d) about 23.50% by weight of microcrystalline
(e) about 14.10% by weight of pregclatinized starch;
(f) about 5% by weight of flavor; and
(g) about 1% by weight of lubricant.

4. A dosage form comprising the composition of claim 1.

* * * * *

UNITED STATES PATENT AND TRADEMARK OFFICE
CERTIFICATE OF CORRECTION

PATENT NO. : 10,668,012 B2  
APPLICATION NO. : 12/554361  
DATED : June 2, 2020  
INVENTOR(S) : Andrew Xian Chen et al.

Page 1 of 1

It is certified that error appears in the above-identified patent and that said Letters Patent is hereby corrected as shown below:

In the Claims

In Column 36, Line 54, Claim 1: delete "wax-Eke" and insert --wax-like--

In Column 38, Line 13, Claim 3: after microcrystalline insert --cellulose--

In Column 38, Line 14, Claim 3: delete "pregclatinized" and insert --pregelatinized--

Signed and Sealed this  
Twenty-ninth Day of September, 2020

Andrei Iancu  
*Director of the United States Patent and Trademark Office*